(12) United States Patent
Nakagawa et al.

(10) Patent No.: US 10,241,564 B2
(45) Date of Patent: Mar. 26, 2019

(54) ELECTRONIC APPARATUS AND METHOD OF DETECTING TAP OPERATION

(71) Applicant: Seiko Epson Corporation, Shinjuku-ku (JP)

(72) Inventors: Ryo Nakagawa, Chiba (JP); Yuichi Takano, Matsumoto (JP); Junichi Otsuka, Chikuma (JP)

(73) Assignee: Seiko Epson Corporation, Tokyo (JP)

( * ) Notice: Subject to any disclaimer, the term of this patent is extended or adjusted under 35 U.S.C. 154(b) by 456 days.

(21) Appl. No.: 14/895,887

(22) PCT Filed: May 27, 2014

(86) PCT No.: PCT/JP2014/002773
§ 371 (c)(1),
(2) Date: Dec. 3, 2015

(87) PCT Pub. No.: WO2014/196156
PCT Pub. Date: Dec. 11, 2014

(65) Prior Publication Data
US 2016/0132102 A1    May 12, 2016

(30) Foreign Application Priority Data

Jun. 7, 2013  (JP) ................................ 2013-120587
Jun. 7, 2013  (JP) ................................ 2013-120588

(51) Int. Cl.
*G06F 3/00*     (2006.01)
*A61B 5/00*     (2006.01)
(Continued)

(52) U.S. Cl.
CPC .......... *G06F 3/002* (2013.01); *A61B 5/02416* (2013.01); *A61B 5/02438* (2013.01);
(Continued)

(58) Field of Classification Search
CPC ........ G06F 3/002; G06F 3/0416; G06F 3/011; G06F 1/325; G06F 1/1694; G06F 1/3265;
(Continued)

(56) References Cited

U.S. PATENT DOCUMENTS

2002/0151775 A1   10/2002   Kondo
2005/0012755 A1   1/2005    Dresevic et al.
(Continued)

FOREIGN PATENT DOCUMENTS

EP    2 491 856 A1    8/2012
JP    2001-086233 A   3/2001
(Continued)

OTHER PUBLICATIONS

Supplementary European Search Report from corresponding European Application No. 14 807 057.6 dated May 31, 2017 (11 pages).

*Primary Examiner* — Stephen G Sherman
(74) *Attorney, Agent, or Firm* — Kilpatrick Townsend & Stockton LLP

(57) ABSTRACT

To provide an electronic apparatus, a method of detecting a tap operation, etc. for performing appropriate detection processing of a tap operation. The electronic apparatus includes a setting unit 110 that sets a sampling frequency for acceleration detection of an acceleration sensor 10, a processing unit 120 that performs a determination of a tap operation based on sensor information from the acceleration sensor 10, an operation information acquisition unit 130 that acquires operation information from an operation unit 140, and a communication unit 150 that performs communication processing of information, wherein, when reception of the information by the communication unit 150 is detected or when acquisition of the operation information by the operation information acquisition unit 130 is detected, the setting
(Continued)

unit 110 sets the sampling frequency to F2 as a higher frequency than the sampling frequency F1 before detection.

16 Claims, 16 Drawing Sheets

(51) Int. Cl.
| | |
|---|---|
| *G06F 1/16* | (2006.01) |
| *G06F 1/3231* | (2019.01) |
| *G06F 1/3234* | (2019.01) |
| *G06F 3/01* | (2006.01) |
| *G06F 3/041* | (2006.01) |
| *A61B 5/024* | (2006.01) |

(52) U.S. Cl.
CPC .............. *A61B 5/681* (2013.01); *A61B 5/721* (2013.01); *A61B 5/7475* (2013.01); *G06F 1/163* (2013.01); *G06F 1/1694* (2013.01); *G06F 1/325* (2013.01); *G06F 1/3231* (2013.01); *G06F 1/3265* (2013.01); *G06F 3/011* (2013.01); *G06F 3/0416* (2013.01); *G06F 2200/1636* (2013.01); *Y02D 10/173* (2018.01)

(58) Field of Classification Search
CPC ................... G06F 1/3231; G06F 1/163; G06F 2200/1636; A61B 5/02438; A61B 5/02416; A61B 5/7475; A61B 5/681; A61B 5/721; Y02D 10/173
See application file for complete search history.

(56) References Cited

U.S. PATENT DOCUMENTS

| | | |
|---|---|---|
| 2005/0172311 A1 * | 8/2005 | Hjelt .................... A61B 5/1112 725/10 |
| 2005/0210417 A1 | 9/2005 | Marvit et al. |
| 2005/0210418 A1 | 9/2005 | Marvit et al. |
| 2005/0212749 A1 | 9/2005 | Marvit et al. |
| 2005/0212750 A1 | 9/2005 | Marvit et al. |
| 2005/0212751 A1 | 9/2005 | Marvit et al. |
| 2005/0212752 A1 | 9/2005 | Marvit et al. |
| 2005/0212753 A1 | 9/2005 | Marvit et al. |
| 2005/0212754 A1 | 9/2005 | Marvit et al. |
| 2005/0212756 A1 | 9/2005 | Marvit et al. |
| 2005/0212757 A1 | 9/2005 | Marvit et al. |
| 2005/0212758 A1 | 9/2005 | Marvit et al. |
| 2005/0212759 A1 | 9/2005 | Marvit et al. |
| 2005/0212760 A1 | 9/2005 | Marvit et al. |
| 2005/0212766 A1 | 9/2005 | Reinhardt et al. |
| 2005/0212767 A1 | 9/2005 | Marvit et al. |
| 2005/0212911 A1 | 9/2005 | Marvit et al. |
| 2005/0216867 A1 | 9/2005 | Marvit et al. |
| 2005/0253806 A1 | 11/2005 | Liberty et al. |
| 2010/0328201 A1 | 12/2010 | Marvit et al. |
| 2011/0050569 A1 | 3/2011 | Marvit et al. |
| 2012/0022382 A1 | 1/2012 | Daisuke et al. |
| 2012/0185203 A1 | 7/2012 | Tanaka |
| 2012/0206414 A1 | 8/2012 | Tada et al. |
| 2013/0229338 A1 * | 9/2013 | Sohn ...................... G06F 3/011 345/156 |
| 2014/0104208 A1 * | 4/2014 | Lee ........................ G06F 3/0416 345/173 |
| 2014/0136867 A1 | 5/2014 | Yamamoto |
| 2014/0168057 A1 * | 6/2014 | Ahuja .................... G06F 3/017 345/156 |
| 2014/0191954 A1 | 7/2014 | Marvit et al. |
| 2014/0309537 A1 | 10/2014 | Niwa et al. |
| 2015/0084904 A1 | 3/2015 | Tada et al. |

FOREIGN PATENT DOCUMENTS

| | | |
|---|---|---|
| JP | 2006-288970 A | 10/2006 |
| JP | 2006-292690 A | 10/2006 |
| JP | 2008-299866 A | 12/2008 |
| JP | 2011-090421 A | 5/2011 |
| JP | 2012-095827 A | 5/2012 |
| JP | 2012-242851 A | 12/2012 |
| JP | 2013-003911 A | 1/2013 |
| WO | 99-440843 A1 | 8/1999 |
| WO | 2012/030477 A1 | 3/2012 |
| WO | 2012/172726 A1 | 12/2012 |
| WO | WO 2013/038296 A1 | 3/2013 |

* cited by examiner

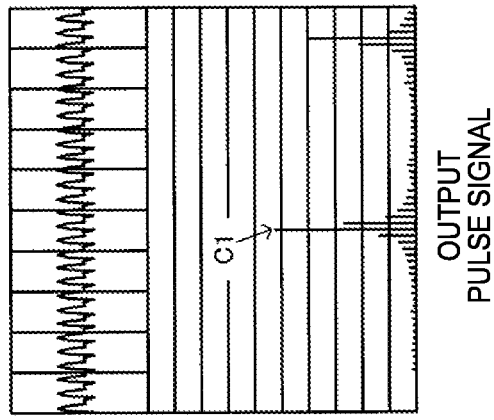
FIG. 6C OUTPUT PULSE SIGNAL
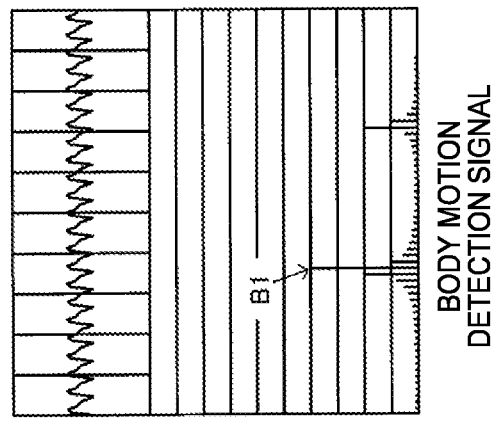
FIG. 6B BODY MOTION DETECTION SIGNAL
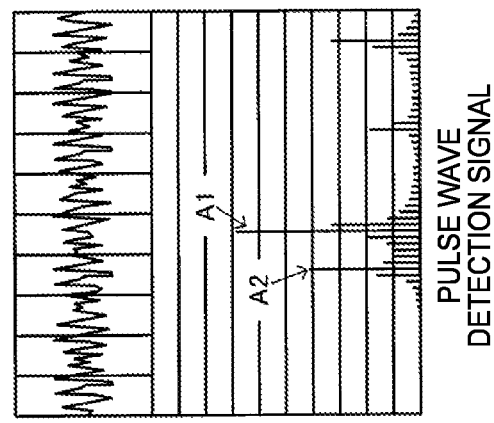
FIG. 6A PULSE WAVE DETECTION SIGNAL

ELECTRONIC APPARATUS AND METHOD OF DETECTING TAP OPERATION

CROSS-REFERENCES TO RELATED APPLICATIONS

This application is a National Phase of international Application No. PCT/JP2014/002773, filed May 27, 2014, which claims priority to Japanese Patent Applications Nos. 2013-120587, filed Jun. 7, 2013, and 2013-120588, filed Jun. 7, 2013, the entireties of which are hereby incorporated by reference

BACKGROUND

Technical Field

This invention relates to an electronic apparatus, a method of detecting a tap operation, etc.

Background Art

Various forms are considered for interfaces for users to input to electronic apparatuses, and may be e.g. an operation unit having keys, buttons, etc. or a touch panel also serving as a display unit. As the other input interfaces, techniques using tap actions (operations) are widely used. Here, the tap action refers to an action of tapping an electronic apparatus by a user using his or her hand or the like, and, in a broader sense, an action of applying an impact to the electronic apparatus. Further, the tap operation refers to operation input by the tap action.

The tap action is a useful user interface in an electronic apparatus in which an input device such as buttons is restricted. For example, in a wristwatch-type electronic apparatus, the buttons or the like are significantly restricted because reduction in size and weight is required and a simple configuration is required for realization of a user-friendly interface.

However, in order to detect the tap action, it is necessary to recognize a very short term of change of acceleration. For example, if sampling of acceleration signals is not performed with resolution of about 200 Hz, the possibility of false detection rises. Note that, the higher the resolution, the higher the power consumption. Namely, accuracy and power consumption have an inverse relation and finding good balance between usability and apparatus battery life is very difficult.

For example, PTL 1 discloses a technique of calculating an amount of activity and changing a detection cycle of an acceleration sensor based on the calculated amount of activity. PTL 1 describes an advantage of reducing power consumption of an activity meter by the technique.

CITATION LIST

Patent Literature

PTL 1: JP-A-2006-288970

SUMMARY OF INVENTION

Technical Problems

The technique of PTL 1 is intended to reduce power consumption of the activity meter and does not consider detection of a tap operation using the acceleration sensor. As described above, in the tap operation, the detection accuracy is lower as the sampling frequency is made lower. Namely, the sampling frequency in the tap operation should be set in view of not only the power consumption but also detection accuracy as to whether the detection status of the tap operation requires higher accuracy or whether the lower accuracy is sufficient, however, PTL 1 does not disclose the view. Particularly, an advantage by setting a threshold value of acceleration used for the detection of the tap operation cooperatively with the sampling frequency may be expected, however, the technique is not shown in PTL 1.

According to some aspects of the invention, an electronic apparatus, a method of detecting a tap operation, etc. for appropriate detection processing of a tap operation may be provided. Further, according to some aspects of the invention, an electronic apparatus, a method of detecting a tap operation, etc. for appropriately setting detection accuracy of the tap operation and power consumption by the detection processing of the tap operation according to operation information, a reception status of a communication unit, etc. may be provided.

Further, according to some aspects of the invention, an electronic apparatus, a method of detecting a tap operation, etc. for performing appropriate detection processing of a tap operation by cooperatively setting the sampling frequency and the threshold value may be provided.

Solution to Problems

An aspect of the invention relates to an electronic apparatus including a setting unit that sets a sampling frequency for acceleration detection of an acceleration sensor, a processing unit that performs a determination of a tap operation based on sensor information from the acceleration sensor, an operation information acquisition unit that acquires operation information from an operation unit, and a communication unit that performs communication processing of information, wherein, when reception of the information by the communication unit is detected or when acquisition of the operation information by the operation information acquisition unit is detected, the setting unit sets the sampling frequency to F2 as a higher frequency than the sampling frequency F1 before detection.

In the aspect of the invention, when the reception of the information by the communication unit or the acquisition of the operation information is detected, the sampling frequency of the acceleration sensor used for the detection of the tap operation is set to be higher. Thereby, in the situation in which it is highly possible that the tap operation is subsequently performed, the sampling frequency may be set to be higher, and the detection of the tap operation or the like with high accuracy in an appropriate situation can be performed. Further, that leads to reduction of the sampling frequency when the possibility of the tap operation is lower, efficient reduction of power consumption or the like can be realized.

Further, in the aspect of the invention, a biological information detection sensor that detects biological information is provided, wherein the processing unit may perform correction processing on biological information from the biological information detection sensor based on body motion information as the sensor information from the acceleration sensor, and perform a determination of the tap operation based on the sensor information from the acceleration sensor.

Thereby, detection processing of the tap operation and noise reduction processing of the biological information or the like can be performed using the common acceleration sensor.

Furthermore, in the aspect of the invention, the processing unit may perform mode switching processing of an operation mode of the electronic apparatus, and the setting unit may perform a setting of changing the sampling frequency from F1 to F2 when the mode switching processing of switching the operation mode of the electronic apparatus from a first mode to a second mode is performed based on the operation information in the processing unit.

Thereby, the setting of the sampling frequency or the like can be performed based on the operation mode of the electronic apparatus.

Moreover, in the aspect of the invention, the first mode may be an information display mode for displaying information, the second mode may be an information input mode for receiving external input of information, and the setting unit may perform a setting of changing the sampling frequency from F1 to F2 when the mode switching processing of switching the operation mode of the electronic apparatus from the information display mode to the information input mode is performed based on the operation information in the processing unit.

Thereby, in the information input mode, the setting of the sampling frequency to be higher than that in the information display mode or the like can be performed.

In addition, in the aspect of the invention, a display control unit that performs display control of information in a display unit is provided, wherein, when the operation mode is the information input mode, the processing unit may perform a determination of the tap operation based on the sensor information from the acceleration sensor in which the sampling frequency is set to F2, and the display control unit may perform the display control of transitioning a displayed image displayed on the display unit when the tap operation is detected in the processing unit.

Thereby, when the tap operation is detected in the information input mode, transition of the displayed image or the like can be performed based on the tap operation.

Further, in the aspect of the invention, when the operation mode is the information input mode and acquisition of the operation information is not detected and the tap operation is not detected in the processing unit for a given period, the processing unit may perform the mode switching processing of switching the operation mode from the information input mode to the information display mode, and the setting unit may perform a setting of changing the sampling frequency from F2 to F1.

Thereby, under a given condition, the mode switching processing from the information input mode to the information display mode can be automatically performed after a lapse of a fixed period, and the setting of the sampling frequency in response to the mode switching processing or the like can be performed.

Another aspect of the invention relates to an electronic apparatus including a setting unit that sets a sampling frequency for acceleration detection of an acceleration sensor, a processing unit that performs a determination of a tap operation based on sensor information from the acceleration sensor, and a wearing determination unit that determines a wearing state of the electronic apparatus, wherein, when the electronic apparatus is determined to be in a non-wearing state, the setting unit sets the sampling frequency to F1 as a lower frequency than the sampling frequency F2 before determination.

In the other aspect of the invention, when the electronic apparatus is in the non-wearing state, the sampling frequency of the acceleration sensor used for the detection of the tap operation is set to be lower. Thereby, in a situation in which it is highly possible that the tap operation is subsequently performed, the sampling frequency may be set to be lower and the efficient reduction of power consumption or the like can be realized.

Another aspect of the invention relates to an electronic apparatus including a setting unit that sets a sampling frequency for acceleration detection of an acceleration sensor and a threshold value for determination of a tap operation, and a processing unit that performs a determination of the tap operation based on sensor information from the acceleration sensor, wherein the setting unit sets the sampling frequency to F1 and sets the threshold value to Th1 in a first set mode of the acceleration sensor, and sets the sampling frequency to F2 as a higher frequency than F1 and sets the threshold value to Th2 as a larger value than Th1 in a second set mode of the acceleration sensor.

In the aspect of the invention, when the setting of the acceleration sensor used for the detection of the tap operation is performed, if the sampling frequency is set to be higher, the threshold value is also set to a larger value. Thereby, appropriate threshold values may be set according to the differences in waveform of acceleration detection values due to differences in sampling frequency, and the setting of the acceleration sensor in consideration of detection accuracy of the tap operation or the like can be performed.

Further, in the aspect of the invention, a biological information detection sensor that detects biological information is provided, wherein the processing unit may perform correction processing on biological information from the biological information detection sensor based on body motion information as the sensor information from the acceleration sensor, and perform a determination of the tap operation based on the sensor information from the acceleration sensor.

Thereby, the detection processing of the tap operation and the noise reduction processing of the biological information or the like can be performed using the common acceleration sensor.

Furthermore, in the aspect of the invention, the setting unit may set the set mode of the acceleration sensor to the second set mode when a user wearing the electronic apparatus is in a motion state.

Thereby, when the user is in the motion state, the setting of the second mode in which the sampling frequency is higher and the threshold value is also larger or the like can be performed.

Moreover, in the aspect of the invention, the setting unit may set the first set mode in an information display mode for displaying information, and sets the second set mode in an information input mode for receiving external input of information.

Thereby, use of appropriate set modes for the respective information display mode and information input mode or the like can be performed.

In addition, in the aspect of the invention, a display control unit that performs display control of information in a display unit is provided, wherein, when the acceleration sensor may be set in the second set mode corresponding to the information input mode by the setting unit, the processing unit may perform a determination of the tap operation based on the sensor information from the acceleration sensor in which the sampling frequency is set to F2 and the threshold value is set to Th2, and the display control unit may perform the display control of transitioning a displayed image displayed on the display unit when the tap operation is detected in the processing unit.

Thereby, when the tap operation is detected in the information input mode, transition of the displayed image or the like can be performed based on the tap operation.

Further, in the aspect of the invention, the processing unit may perform a determination of the tap operation based on at least one comparison processing of comparison processing between a signal value in a positive direction in predetermined axis directions of the acceleration sensor and Th+ as the threshold value in the positive direction and comparison processing between the signal value in a negative direction in the predetermined axis directions of the acceleration sensor and Th− as the threshold value in the negative direction.

Thereby, the detection of the tap operation or the like can be performed based on the comparison processing between fluctuations in vertical directions of the waveform of the acceleration detection values by the tap operation and the set threshold value.

Furthermore, in the aspect of the invention, a wearing determination unit that determines a wearing state of the electronic apparatus is provided, wherein, when the electronic apparatus is determined to be in a non-wearing state by the wearing determination unit, the setting unit may set the acceleration sensor in a third set mode in which a value of the sampling frequency is F0 as a lower frequency than F1.

Thereby, when the electronic apparatus is in the non-wearing state, the setting of the third set mode in which the sampling frequency is the lower frequency than that of the first set mode or the like can be performed.

Another aspect of the invention relates to a method of detecting a tap operation including performing setting processing of setting a sampling frequency for acceleration detection of an acceleration sensor, and performing tap determination processing of determining a tap operation based on sensor information from the acceleration sensor with the set sampling frequency, as the setting processing, when reception of the information by a communication unit is detected or when acquisition of operation information is detected, performing processing of setting the sampling frequency to F2 as a higher frequency than the sampling frequency F1 before detection.

Another aspect of the invention relates to a method of detecting a tap operation including performing setting processing of setting a sampling frequency for acceleration detection of an acceleration sensor, performing tap determination processing of determining a tap operation based on sensor information from the acceleration sensor with the set sampling frequency, as the setting processing, performing a determination of a wearing state of the electronic apparatus, and, when the electronic apparatus is determined to be in a non-wearing state, performing processing of setting the sampling frequency to F1 as a lower frequency than the sampling frequency F2 before determination.

Another aspect of the invention relates to a method of detecting a tap operation including performing setting processing of setting a sampling frequency for acceleration detection of an acceleration sensor and a threshold value for determination of a tap operation, and performing tap determination processing of determining the tap operation based on sensor information from the acceleration sensor with the set sampling frequency and threshold value, as the setting processing, performing processing of setting the sampling frequency to F1 and setting the threshold value to Th1 in a first set mode of the acceleration sensor, and setting the sampling frequency to F2 as a higher frequency than F1 and setting the threshold value to Th2 as a larger value than Th1 in a second set mode of the acceleration sensor.

BRIEF DESCRIPTION OF DRAWINGS

FIGS. 6(A) to 6(C) show examples of waveforms and frequency spectra of pulse wave detection signals, motion detection signals, signals after body motion noise reduction processing based thereon.

DESCRIPTION OF EMBODIMENTS

As below, the embodiment will be explained in detail. Note that the embodiment explained as below does not unduly limit the invention described in claims, and not all of the configurations explained in the embodiment are necessarily the essential component elements of the invention.

1. Technique of Embodiment

First, a technique of the embodiment will be explained. Various forms are considered for interfaces for users to input to electronic apparatuses. In electronic apparatuses of home appliances or the like, physically provided buttons, keys, etc. are generally used. Further, recently, touch panels have been increasingly used as user interfaces, and often used in electronic apparatuses including smartphones.

However, in electronic apparatuses with restricted sizes or the like, it may be considered difficult to provide the above described buttons, touch panels, etc. For example, in wristwatch-type electronic apparatuses, reduction in size and weight is often required and, in this case, it is impossible to provide sufficient numbers of physical buttons and the areas of the touch panels are restricted, and thus, useful interfaces are not obtained.

Further, in those electronic apparatuses, if physical buttons are provided, it is difficult to present the functions of the respective buttons to users in an easy-to-understand manner. For example, in an electronic apparatus such as a television, for the respective buttons provided on the main body and the remote, characters and pictures show that the buttons are for operation of power supply, operation of reproduction, and adjustment of sound volume, and thereby, the user can appropriately operate the many buttons. On the other hand, in the wristwatch-type electronic apparatus or the like, it is necessary to downsize the buttons themselves and, when a plurality of the buttons are provided, it is difficult to clearly show the functions of the respective buttons to the user. As a solution thereto, realization of a user friendly interface by reducing the number of buttons is conceivable, however, the number of types of operations that can be performed by the user is smaller.

Figure 1:
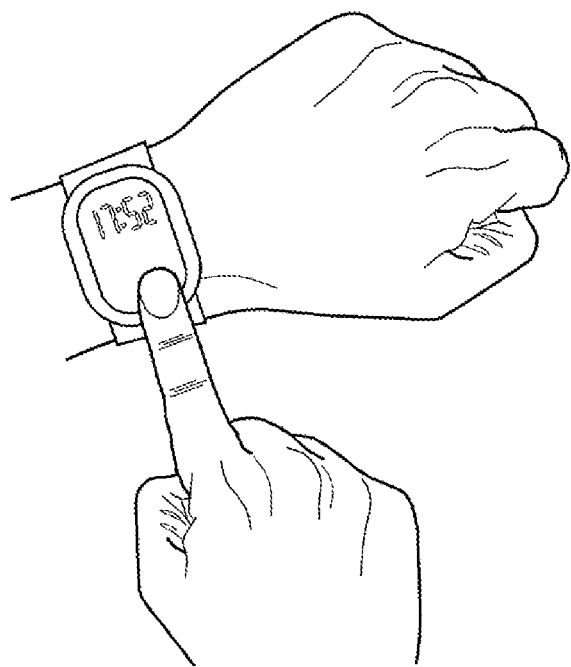
FIG. 1 is an explanatory diagram of a tap operation.

Accordingly, a tap operation is useful. The tap operation is an operation of tapping the electronic apparatus, e.g., in a wristwatch-type electronic apparatus, as shown in FIG. 1, an operation of tapping the electronic apparatus with the opposite hand to the hand wearing the electronic apparatus is attached. Note that, though the tap action with a finger is shown in FIG. 1, the tap operation includes an operation of tapping the electronic apparatus in another way of using the palm or the like.

In the tap operation, the tapping of the apparatus is detected based on sensor information of an acceleration sensor, and thereby, it is not necessary to separately provide a structure for tap operation detection in the electronic apparatus and the tap operation can be used in the above described wristwatch-type electronic apparatus or the like.

Figure 14A:
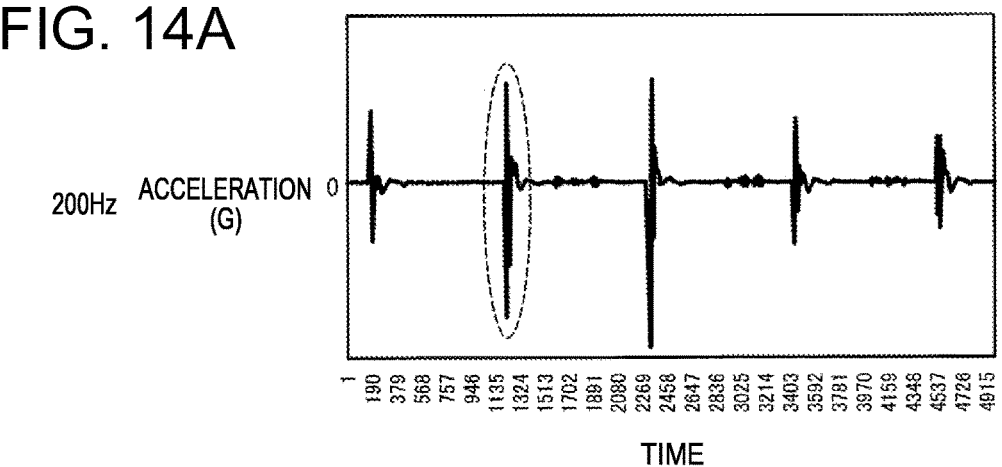
FIGS. 14(A) and 14(B) show waveform examples at a lower sampling frequency.
Figure 14B:
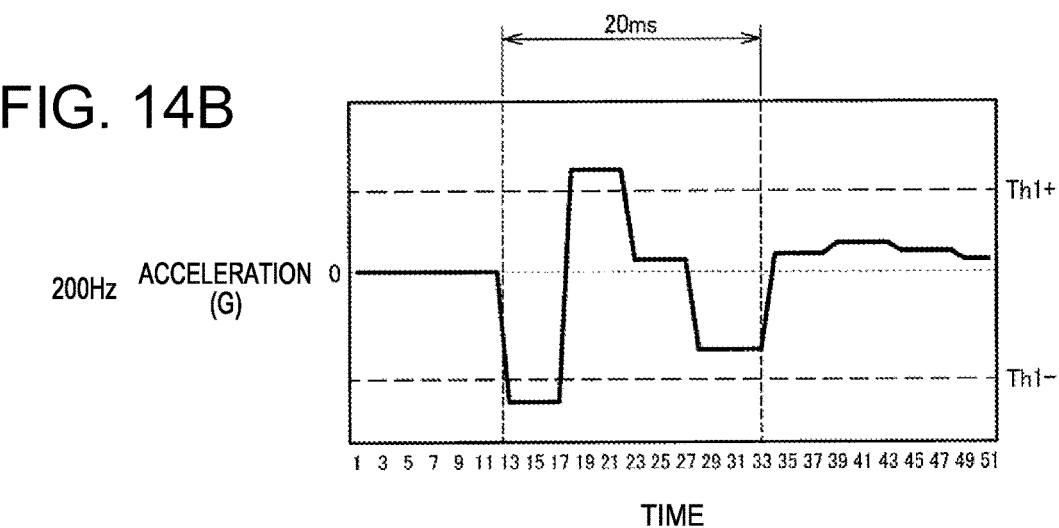

However, to detect the tap operation, it is necessary to detect a change in acceleration in a very short period. The details will be described later, and, for example, as shown in FIG. 14B, it is necessary to detect fluctuations in vertical directions of an acceleration signal waveform in 20 ms. In a study made by the applicant, it is known that, as a specific numeric value, the sampling frequency of at least about 200 Hz is required. Further, as the sampling frequency is set to be higher, the detection accuracy of the tap operation is more improved. In a study made by the applicant, it is known that the false detection of the tap operation may be sufficiently reduced using the sampling frequency of about 1620 Hz.

That is, in a numeric value range to some degree, as the sampling frequency is set to be higher, there is an advantage that the detection accuracy of the tap operation is higher and, on the other hand, there is a disadvantage that power consumption is larger. Particularly, as an electronic apparatus in which the tap operation is useful, the above described compact and portable electronic apparatus is assumed, and higher power consumption is an significant problem in consideration of the restriction of battery capacity or the like. Namely, the detection accuracy and the power consumption have an inverse relation, and it is necessary to find good balance between usability and apparatus battery life.

PTL 1 discloses the technique of calculating the amount of activity and changing the detection cycle of the acceleration sensor based on the calculated amount of activity. However, the technique of PTL 1 is intended to reduce power consumption of the activity meter and does not consider detection of the tap operation using the acceleration sensor. As described above, in the tap operation, the detection accuracy is lower as the sampling frequency is made lower. Namely, the sampling frequency in the tap operation should be set in view of detection accuracy as to whether the detection status of the tap operation requires higher accuracy or whether the lower accuracy is sufficient, however, PTL 1 does not disclose the view.

Accordingly, the applicant proposes a technique of appropriately controlling the detection accuracy of the tap operation and the power consumption required for the detection of the tap operation by setting the sampling frequency in consideration of the possibility of the tap operation. Specifically, the sampling frequency is set according to operation information, a reception status of a communication unit, etc. In this manner, an appropriate setting of the acceleration sensor can be performed depending on the tap operation.

Further, the applicant proposes a technique of setting a threshold value used for the detection of the tap operation cooperatively with the sampling frequency. The threshold value is set to correspond to the sampling frequency, and tap operation detection processing suitable for the respective sampling frequencies can be performed. Specifically, when the sampling frequency is higher, the threshold value is also made higher, and thereby, the possibility of false detection of the acceleration detection value caused by another than the tap operation as the tap operation is suppressed. Or, when the sampling frequency is lower, the threshold value is also made lower, and thereby, the possibility of false detection as a non-tap operation even when the tap operation is performed is suppressed.

As below, a system configuration example of the electronic apparatus according to the embodiment will be explained, and then, a technique of detecting the tap operation using the acceleration sensor will be explained. Then, a technique of setting the sampling frequency and a technique of setting the threshold value of tap operation detection according to the setting of the sampling frequency will be explained, and finally, specific examples of the embodiment will be summarized.

2. System Configuration Example

Figure 2:
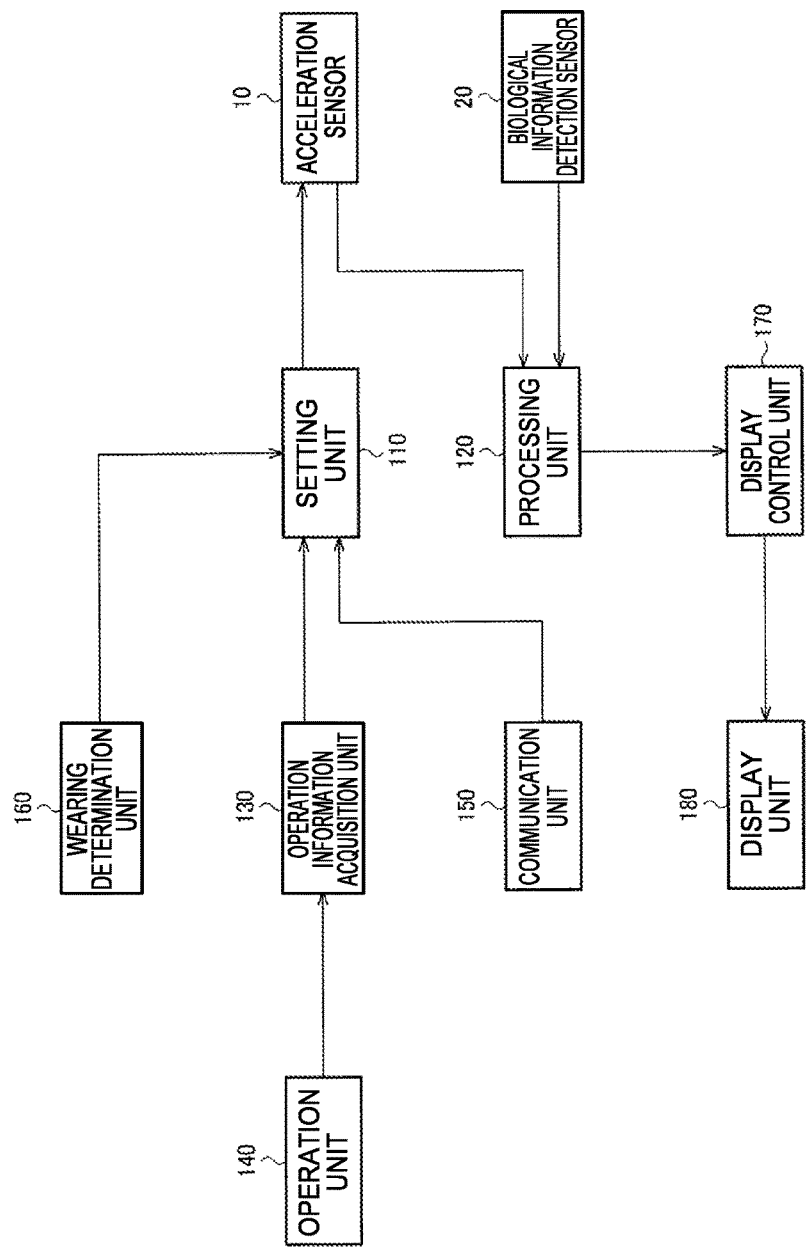
FIG. 2 shows a system configuration example of an electronic apparatus according to the embodiment.

FIG. 2 shows a system configuration example of the electronic apparatus according to the embodiment. As shown in FIG. 2, the electronic apparatus includes an acceleration sensor 10, a biological information detection sensor 20, a setting unit 110, a processing unit 120, an operation information acquisition unit 130, an operation unit 140, a communication unit 150, a wearing determination unit 160, a display control unit 170, and a display unit 180. Note that the electronic apparatus is not limited to the configuration in FIG. 2, and various modifications by omitting part of these component elements or adding another component element can be embodied.

Figure 7A:
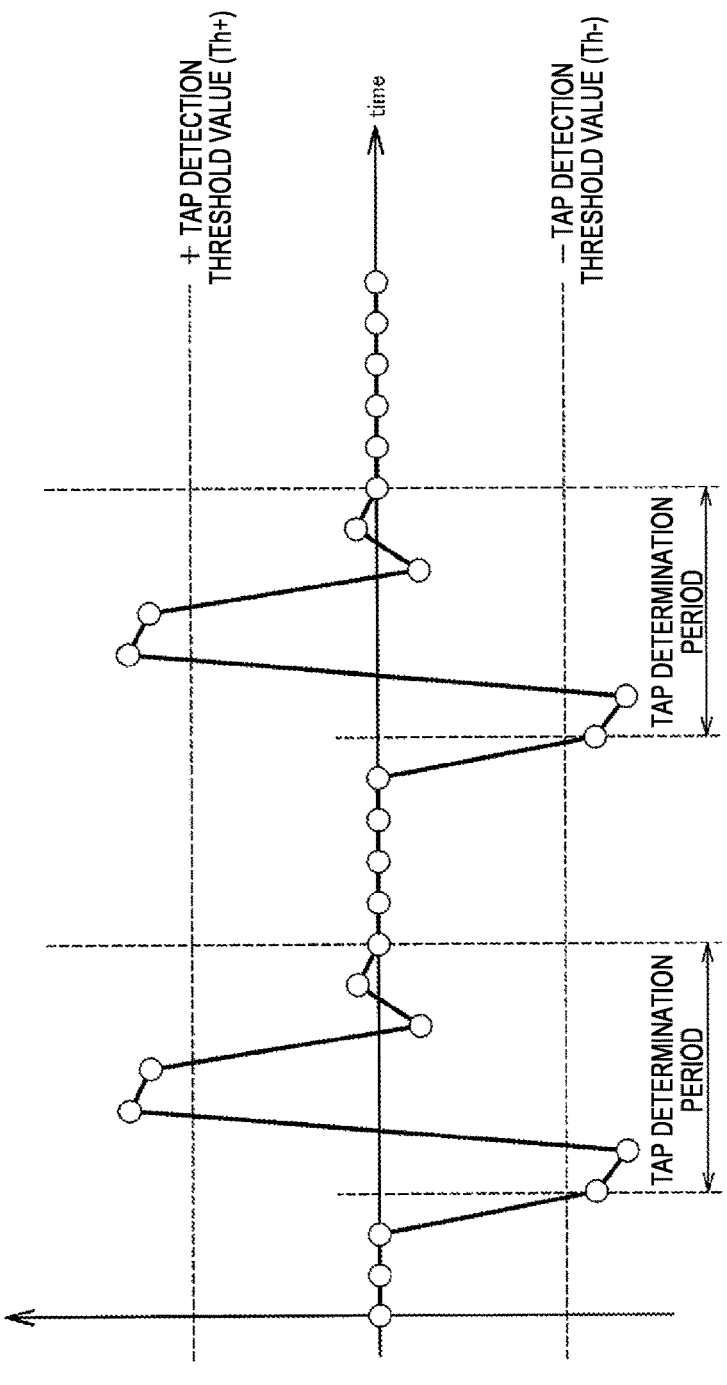
FIG. 7A shows a waveform example of acceleration detection values.
Figure 7B:
FIG. 7B shows a waveform example representing a detection result of a tap operation based on the acceleration detection values.

The acceleration sensor 10 is a sensor that acquires information on acceleration. The acceleration sensor 10 may be e.g. a three-axis acceleration sensor, and more specifically, may be a sensor provided on a wristwatch-type electronic apparatus and detecting acceleration values on respective axes of X-axis, Y-axis, and Z-axis shown in FIG. 3. Specific example of acceleration detection values on a given axis are those as will be described later in FIG. 7(A). Note that the acceleration sensor 10 of the embodiment is not limited to one that outputs values of FIG. 7(A) or the like as they are, but may be one that performs detection processing of a tap operation based on the values of FIG. 7(A) and a parameter set in the setting unit 110, which will be described later, and outputs a result of the detection processing. It is considered that the result of the detection processing of the tap operation is e.g. a pulse waveform of the signals rising at the times corresponding to the detection times as shown in FIG. 7(B).

The biological information detection sensor 20 may be e.g. a pulse wave sensor that detects pulse wave signals, and more specifically, a photoelectric sensor or the like is considered. The electronic apparatus of the embodiment may have not only a simple clock display function but also a function of detecting biological information including pulse wave information of a wearer, and the biological information detection sensor 20 is used in such a case. In this case, the electronic apparatus of the embodiment corresponds to e.g. a pulsimeter or the like. The biological information detection sensor 20 can be omitted when an electronic apparatus not aimed at detection of biological information is intended.

Figure 4:
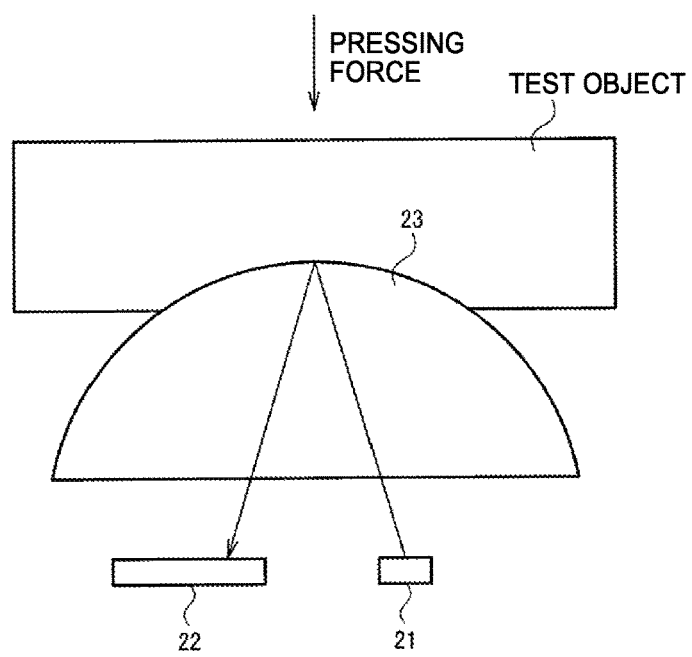
FIG. 4 shows a configuration example of a biological information detection sensor.

FIG. 4 is a schematic diagram in which a part containing the biological information detection sensor of the electronic apparatus is enlarged. As shown in FIG. 4, the biological information detection sensor 20 includes an LED 21 that radiates light, a photodiode (PD) 22 that receives reflected light by reflection by a living organism of the radiated light, and a convex portion 23 as a contact portion with the living organism. The biological information detection sensor 20 of the embodiment has the convex portion 23 shown in FIG. 4, and thereby, effectively applies pressure (pressing force) to the living organism. Here, it is known that, when pulse wave information is detected, the pressing force representing the pressure on the living organism near the pulse wave sensor is adjusted, and thereby, the detection accuracy can be improved. The convex portion 23 in FIG. 4 has a structure in consideration of pressing force adjustment, however, the detailed explanation is omitted because the technique relating to the pressing force adjustment is different from the main purpose of the technique of the embodiment.

The setting unit 110 sets a parameter in the detection processing of the tap operation using the acceleration sensor 10 based on information from the operation information acquisition unit 130, the communication unit 150, the wearing determination unit 160, etc., which will be described later. Specifically, the sampling frequency and the threshold value of the acceleration signals are set. The details of the setting processing in the setting unit 110 will be described later.

The processing unit 120 performs various kinds of processing based on sensor information from the acceleration sensor 10. Specifically, the processing unit 120 performs the detection processing of the tap operation, noise reduction processing on the biological information from the biological information detection sensor 20, and mode switching processing of switching operation modes of the electronic apparatus. The detection processing of the tap operation does not hinder performance of comparison processing between the acceleration signal values and the threshold value, which will be described later. Note that, when the pulse signal shown in FIG. 7(B) is output from the acceleration sensor 10 as described above, the comparison processing with the threshold value is performed in the acceleration sensor 10, and the processing in the processing unit 120 is determination processing as to whether or not there is a pulse in the sensor information from the acceleration sensor 10.

Further, it is known that, when the electronic apparatus performs detection processing of biological information, the sensor information from the biological information detection sensor 20 (biological information detection signal) includes body motion noise caused by motion of the user or the like. Accordingly, the processing unit 120 may perform processing of reducing the body motion noise from the biological information detection signal using the sensor information from the acceleration sensor 10 as a body motion detection signal. It is assumed that the sensor information from the acceleration sensor 10 in this case is not FIG. 7(B), but FIG. 7(A) representing the signal values.

Figure 5:
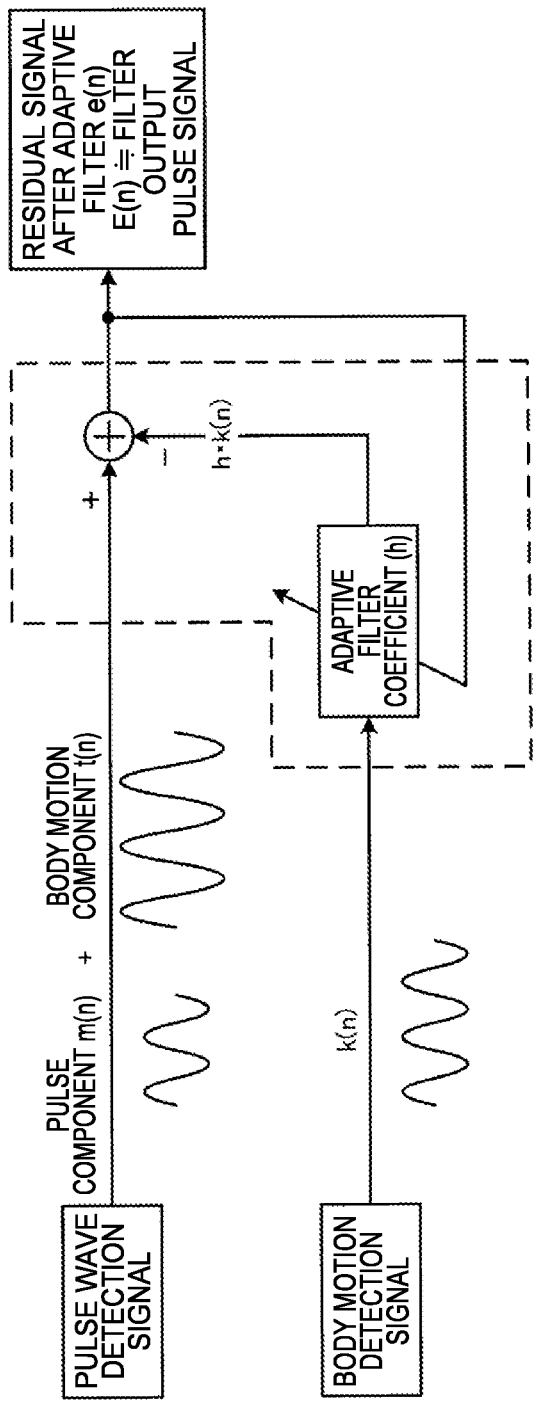
FIG. 5 shows an example of body motion noise reduction processing using an adaptive filter.

A specific example of the noise reduction processing using an adaptive filter is shown in FIG. 5. The sensor information acquired from the biological information detection sensor 20 (in a narrow sense, a pulse wave detection signal) includes not only a component due to heartbeat but also a component due to body motion. Of them, what is useful for calculation of the pulse rate or the like is the component due to heartbeat, and the component due to body motion hinders the calculation. Accordingly, the acceleration sensor 10 is used as a body motion sensor to acquire a signal due to body motion (body motion detection signal) and a signal component correlated to the body motion detection signal (referred to as "estimated body motion noise component") from the pulse wave detection signal is removed, and thereby, the body motion noise contained in the pulse wave detection signal is reduced. Note that the body motion noise in the pulse wave detection signal and the body motion detection signal from the body motion sensor do not necessarily have the same signal level because they are the signals due to the same body motion. Accordingly, filter processing for which a filter coefficient is adaptively determined with respect to the body motion detection signal is performed, and thereby, the estimated body motion noise component is calculated and a difference between the pulse wave detection signal and the estimated body motion noise component is obtained.

The explanation of the above described processing using frequency spectra is as shown in FIGS. 6(A) to 6(C). FIG. 6(A) etc. show time-varying waveforms of signals in upper parts and frequency spectra in lower parts. FIG. 6(A) shows a pulse wave detection signal before body motion noise reduction, and, as shown by A1 and A2, two frequencies having larger values appear in the spectrum. Of them, one is due to heartbeat and the other is due to body motion. Note that some higher frequencies than A1 having larger values are not considered because they are high-frequency components corresponding to integral multiples of A1, A2. As below, some high-frequency components also appear in FIGS. 6(B), 6(C), however, they are not considered here.

In contrast, FIG. 6(B) shows a body motion signal and, if one kind of body motion causes the body motion detection signal, one frequency having the larger value appears as shown by B1. Here, the frequency of B1 corresponds to A2 in FIG. 6(A). In this case, a difference between the pulse wave detection signal and the estimated body motion noise component is obtained using the technique as shown in FIG. 5, and thereby, a signal in FIG. 6(C) is obtained. As is clear from the graphs, the estimated body motion noise component having the peak B1 due to body motion is subtracted from the pulse wave detection signal having the two peaks A1, A2 due to heartbeat and body motion, and thereby, the body motion component (corresponding to A2) in the pulse wave detection signal is removed and, consequently, the peak C1 (having the frequency corresponding to A1) due to heart beat is left.

The operation information acquisition unit 130 acquires operation information from the operation unit 140. The operation unit 140 represents a user interface including buttons, keys, or a touch panel. The operations by the operation unit 140 do not include the tap operation as a target in the embodiment. Note that, the operation information here is information representing operations by the user for the operation unit 140, and may be e.g. information that which button is pressed down or a control signal formed based on a specific key operation for allowing the electronic apparatus to execute specific control.

The communication unit 150 performs communication processing of information with another electronic apparatus or the like via a network. The network here may be in wired or wireless connection. For example, it is considered that, when the electronic apparatus of the embodiment is a wristwatch-type device, the wristwatch-type device and a smartphone or the like are connected via a network of short-range wireless connection or the like, and they interlockingly operate while communicating information. The communication unit 150 serves as an interface in this regard, and acquires information of e.g. the operation of the smartphone by the user, reception of information by the smartphone, or the like from the smartphone.

The wearing determination unit 160 determines a wearing state of the electronic apparatus and outputs a determination result to the setting unit 110. For example, when the electronic apparatus includes the biological information detection sensor 20 having the photodiode 22 as shown in FIG. 4, the wearing determination may be performed based on an amount of light detected by the photodiode 22. Generally, when the pulse wave signal is detected, while outside light is blocked or, even when outside light is slightly detected, its value is made smaller to the extent that can be cancelled out, the reflected light and the transmitted light of the light from the LED 21 are detected. However, this is on the assumption that the biological information detection sensor 20 is used in close contact with a test object. Accordingly, for example, when the electronic apparatus is in a non-wearing state such that the wristwatch-type electronic apparatus is detached from an arm, outside light is detected by the photodiode 22. Further, it is known that the outside light is very strong light compared to the reflected light and the transmitted light of the light from the LED 21. Namely, the amount of light detected by the photodiode 22 in the non-wearing state is very large compared to that in the wearing state, and the wearing determination can be performed with attention focused on the point. Note that another technique may be used for the wearing determination, and various modifications can be embodied. As an example, the acceleration detection values in the acceleration sensor 10 may be used. For example, larger values by walking and swinging of the arm are detected in wearing, and, on the other hand, when the apparatus is left on a desk or the like in the non-wearing state, other values than gravitational acceleration are rarely detected. The wearing determination may be performed based on the difference.

The display control unit 170 performs control of the display unit 180. The display unit 180 is for display of various display screens and may be realized by e.g. a liquid crystal display or an organic EL display. Note that the display unit 180 is not limited to that contained in the electronic apparatus, but may be provided in another apparatus connected to the electronic apparatus such as a smartphone.

3. Basic Technique for Tap Detection

Next, a basic technique for detecting the tap operation based on the acceleration detection values detected by the acceleration sensor 10 will be explained. In the tap operation, the tap action as shown in FIG. 1 is performed, and an impact by the action is detected in the acceleration sensor 10.

It is known that the impact by the tap action is detected as fluctuations in vertical directions of the signal waveform as shown in FIG. 7(A) in the acceleration detection values of the acceleration sensor 10. Accordingly, in the embodiment, the detection of the tap operation is performed based on comparison processing between the downward signal value and the threshold value, comparison processing between the upward signal value and the threshold value, or comparison processing of both. In the following explanation, the downward signal value is used, however, the same processing may be performed on the upward signal value. Further, when both upward and downward signal values are used, the tap operation may be detected if both exceed the threshold value or the tap operation may be detected if at least one of them exceeds the threshold value.

3.1 Setting in Predetermined Axis Directions of Acceleration Sensor

The waveform shown in FIG. 7(A) shows changes of the signal values in predetermined axis directions of the acceleration sensor 10. Here, it is considered that the impact by the tap operation is detected most strongly on the axis in the direction in which the impact is applied. For example, when the face part of the watch-type device is tapped from above as shown in FIG. 1, a strong impact is applied with respect to the axis in the direction of penetration of the face part from above to below. Accordingly, as the axis for the detection of the tap operation, the axis in the impact direction may be used.

Figure 3:
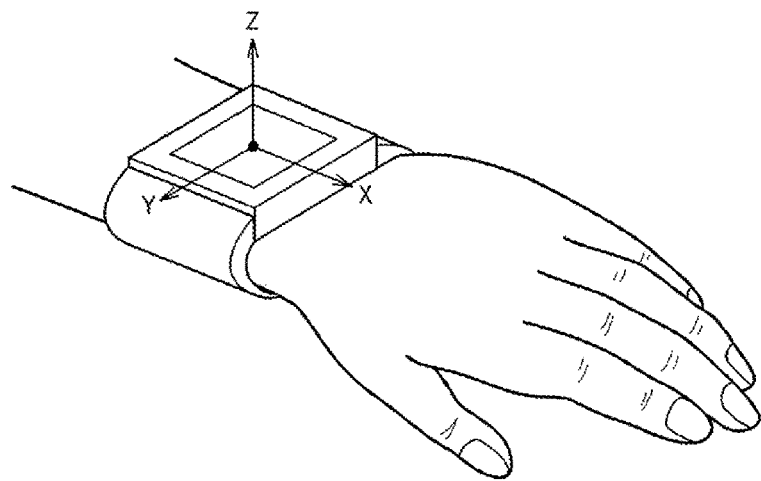
FIG. 3 shows a setting example of axes of an acceleration sensor.

For example, it is assumed that the acceleration sensor 10 detects acceleration with respect to at least three axes and the three axes are set in directions with respect to the watch-type device as shown in FIG. 3. In this case, an impact is applied in a negative direction of the Z-axis, and changes of signal values on the Z-axis may be used. Specifically, it is considered that the signal waveform on the Z-axis is as shown in FIG. 7(A). Note that, the impact is not only applied in the negative direction of the Z-axis, but acceleration detection values representing impacts may be acquired with respect to the X-axis and the Y-axis. Accordingly, the detection of the tap operation may be performed using not only the Z-axis but also the other axes. In this case, determination processing using the X-axis, determination processing using the Y-axis, and determination processing using the Z-axis may be independently performed and a final detection determination may be made based on the results thereof, or determination processing may be performed by composition of values on the X-axis, the Y-axis, and the Z-axis (for example, forming a resultant vector representing acceleration and using the magnitude of the resultant vector).

Further, the relationship between the directions of the respective axes of the acceleration sensor 10 and the electronic apparatus is not necessarily as shown in FIG. 3, and it depends on the direction in which the acceleration sensor 10 is attached in the electronic apparatus. In this case, none of the axes of the acceleration sensor 10 coincides with the axis assumed to be in the direction of the impact (in a narrow sense, the axis in the direction of penetration of the face part from above to below). Various kinds of processing may be considered in this case. For example, the acceleration value on the axis assumed to be in the direction of the impact may be calculated using the values on the X-axis, the Y-axis, and the Z-axis and the determination processing may be performed using the result of the calculation. In this case, that corresponds to acquisition of one resultant vector by composition of the three acceleration vectors represented by the respective values on the X-axis, the Y-axis, and the Z-axis, and processing using the magnitude of a projection vector obtained by projection of the resultant vector in the direction of the impact. Or, regardless of the direction of the impact, the determination processing may be performed using the magnitude of the resultant vector without change. Or, as described above, the determination processing may be performed independently with respect to each axis and the final determination processing may be performed based on the results.

In the specification, "the predetermined axis directions of the acceleration sensor" may be directions of an axis specified by one of the above described various techniques. For convenience, in the following explanation, the direction of the Z-axis shown in FIG. 3 are "the predetermined axis directions of the acceleration sensor", but not limited to those.

3.2 Distinction Processing Between Tap Operation and Similar Actions

Figure 8A:
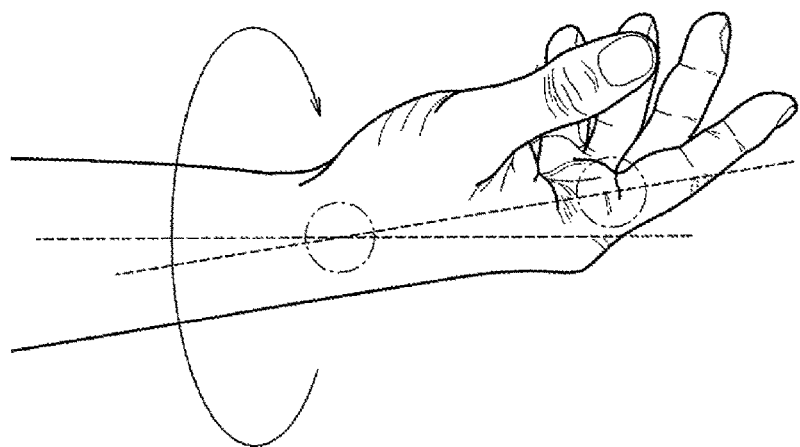
FIGS. 8(A) and 8(B) show actions with waveforms of acceleration detection values having resemblances to tap operations.
Figure 8B:
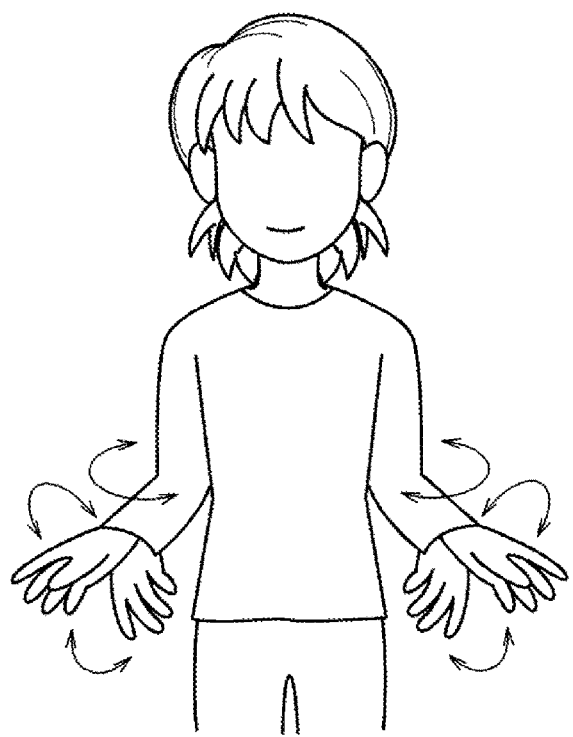

As shown in FIG. 7(A), in the tap operation, large changes in acceleration appear in vertical directions, and it is only necessary to detect the changes. However, there are other actions for which changes in acceleration appear in vertical directions than the tap operation. Specifically, there are an action of turning a wrist as shown in FIG. 8(A) and an action of flexing a wrist as shown in FIG. 8(B).

Figure 9A:
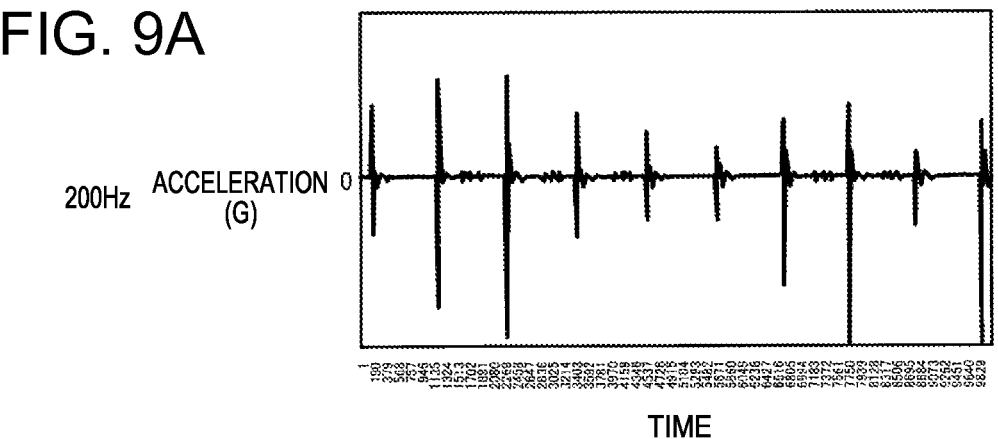
FIGS. 9(A) to 9(C) show waveform examples of acceleration detection values by tap operations at different sampling frequencies.
Figure 9B:
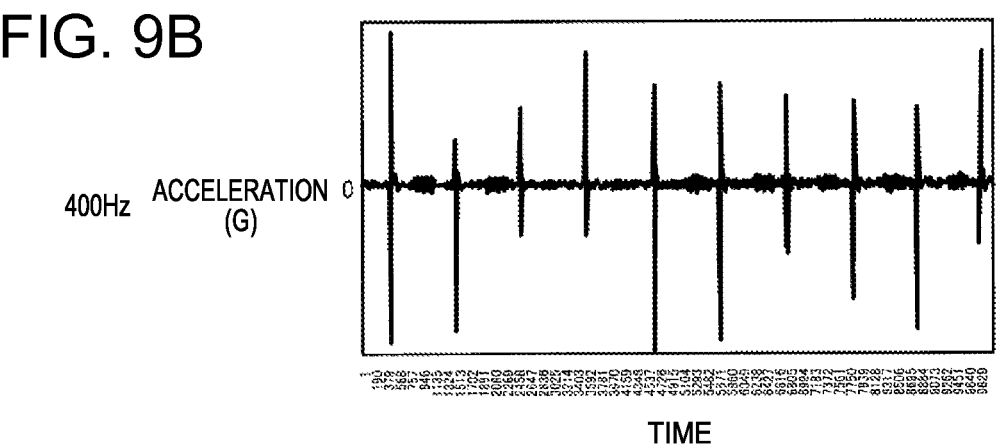
Figure 9C:
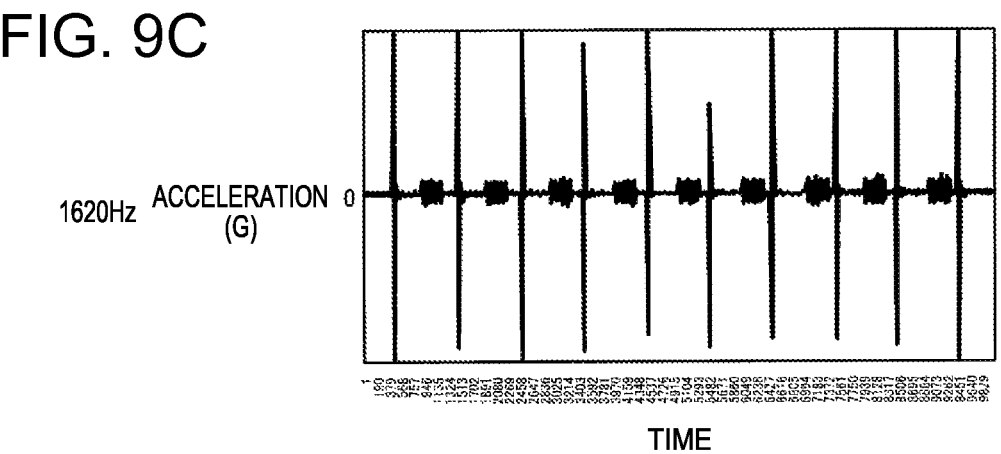
Figure 10A:
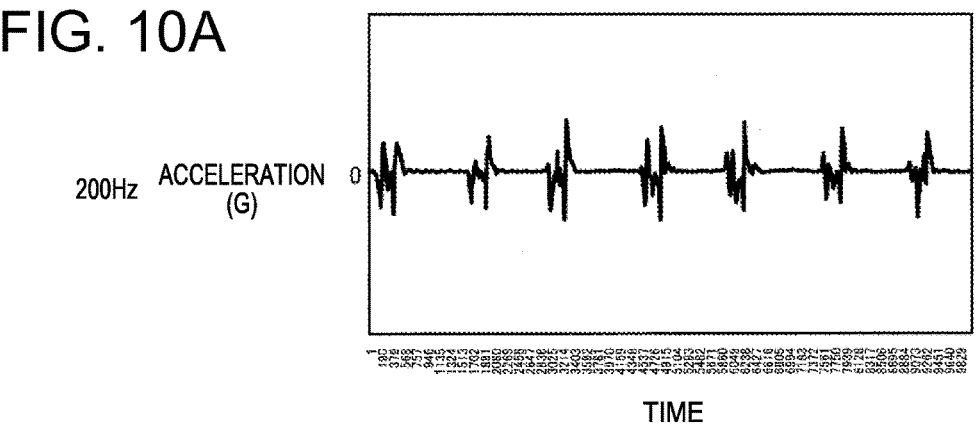
FIGS. 10(A) to 10(C) show waveform examples of acceleration detection values by turning actions of a wrist at different sampling frequencies.
Figure 10B:
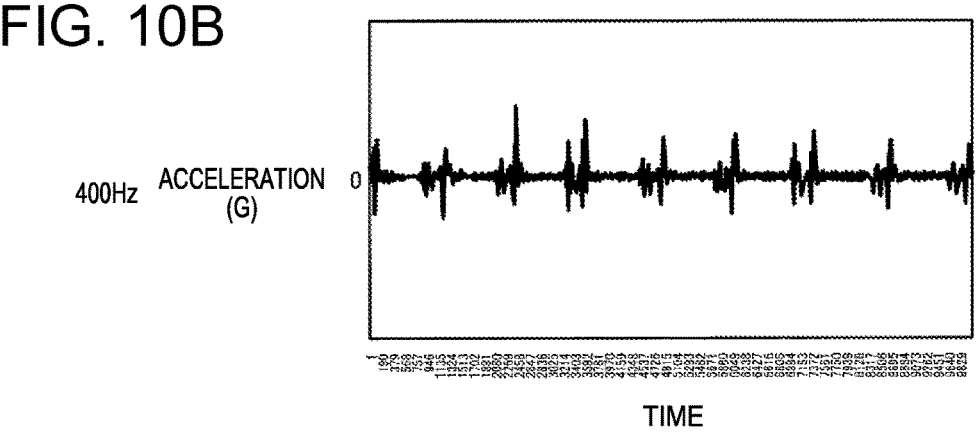
Figure 10C:
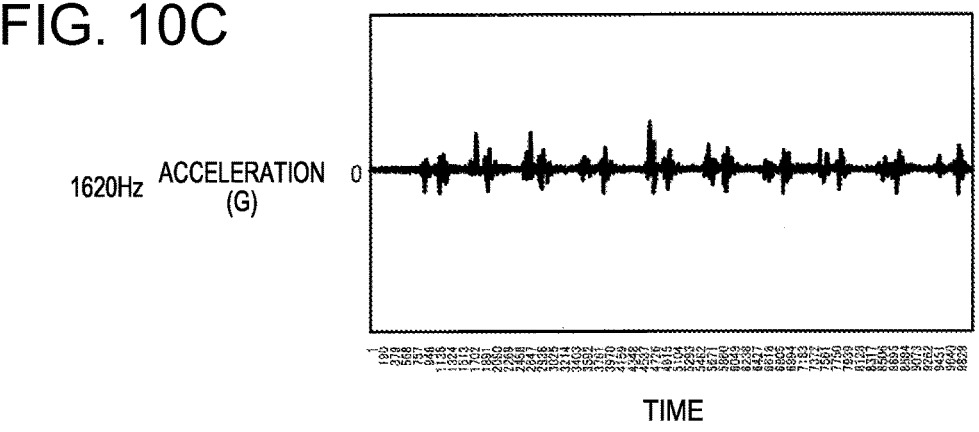
Figure 11A:
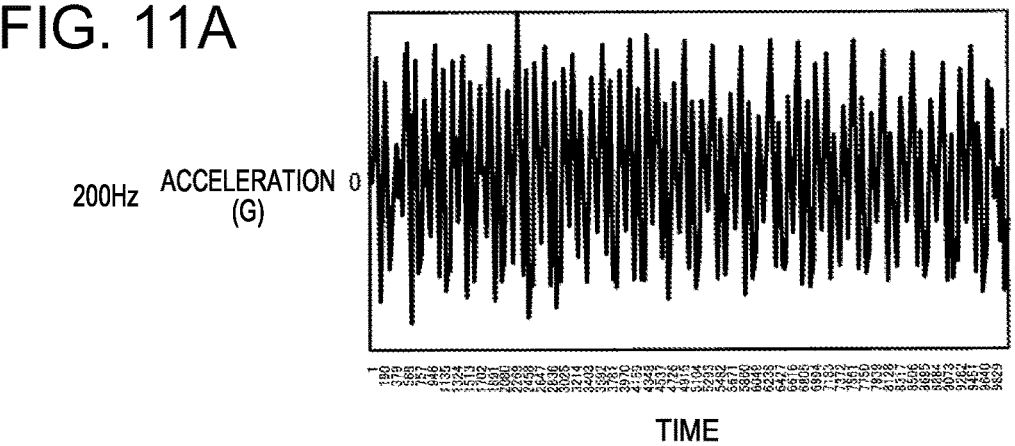
FIGS. 11(A) to 11(C) show waveform examples of acceleration detection values by flexing actions of a wrist at different sampling frequencies.
Figure 11B:
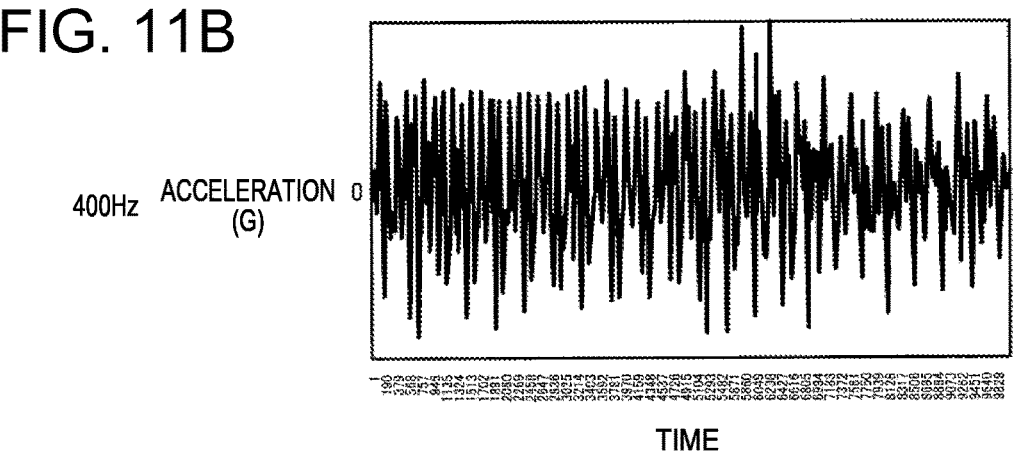
Figure 11C:
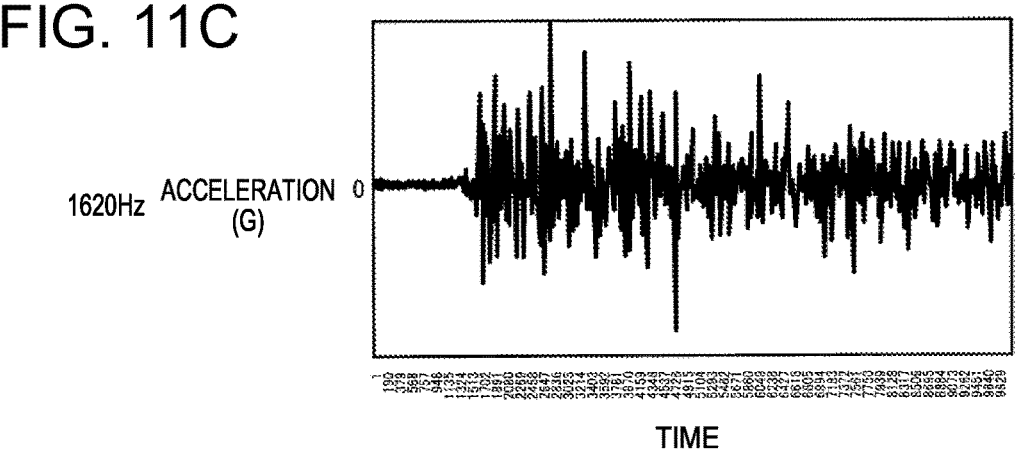

FIGS. 9(A) to 9(C) show changes of acceleration detection values of tap operations at different sampling frequencies. The specific sampling frequencies are 200 Hz in FIG. 9(A), 400 Hz in FIG. 9(B), and 1620 Hz in FIG. 9(C). The same applies to FIGS. 10(A) to 10(C) and FIGS. 11(A) to 11(C). Further, FIGS. 10(A) to 10(C) show changes of acceleration detection values of a turning action of a wrist, and FIGS. 11(A) to 11(C) show changes of acceleration detection values of a flexing action of a wrist. As known from FIG. 9(A) to 11(C), all of them are the same in that the acceleration detection values change in vertical directions. In order to accurately detect the tap operation, it is necessary to appropriately distinguish the turning action of the wrist, the flexing action of the wrist, and the tap operation.

Figure 12A:
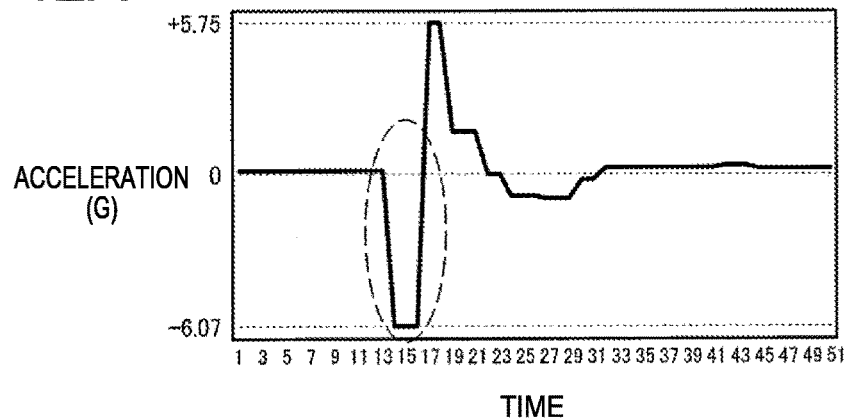
FIGS. 12(A) to 12(C) show waveform examples of acceleration detection values by a tap operation, a turning action of a wrist, and a flexing action of a wrist in relatively short periods.
Figure 12B:
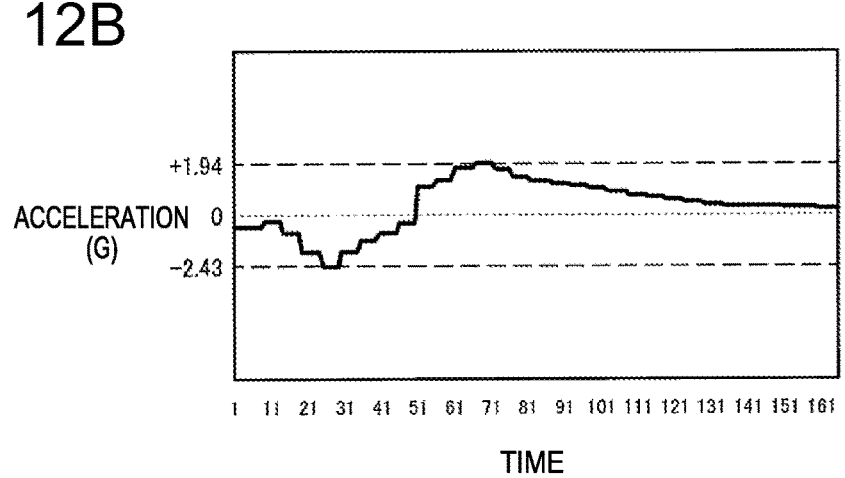
Figure 12C:
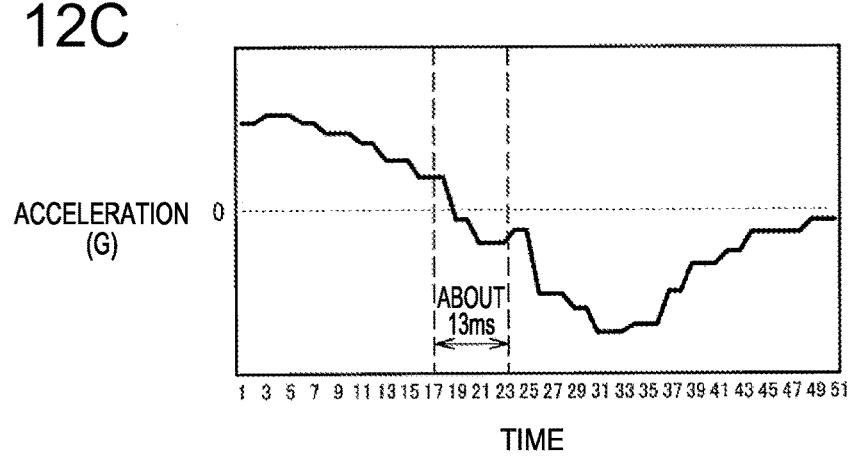

FIGS. 12(A) to 12(C) show acceleration changes in a relatively short period of the respective tap operation, turning action of the wrist, and flexing action of the wrist. The sampling frequency in FIGS. 12(A) to 12(C) is set to 400 Hz.

FIG. 12(A) shows a waveform of the acceleration detection values by the tap operation, and it is known that the range of the fluctuations of acceleration in vertical directions is about −6 G to +5.7 G in the tap operation. Note that, here, the explanation is made by assuming that the acceleration value without the tap operation is 0 G. Further, as is known from the area surrounded by a dotted line in FIG. 12(A), the acceleration change in one direction has a length of about 10 to 13 ms and one period of the fluctuations in vertical directions has a length of about 20 to 26 ms.

Compared with the waveform changes of the turning action of the wrist in FIG. 12(B) in light of that, in the turning action of the wrist, the range of the fluctuations in vertical directions is relatively small and is about −2.4 G to +1.9 G. Namely, by providing a threshold value between −6 G to −2.4 G for determinations in the negative direction and between +1.9 G to +5.7 G for determinations in the positive direction, the tap operation and the turning action of the wrist can be distinguished based on comparison processing between the threshold value and the acceleration detection values.

On the other hand, when the tap operation is compared with the waveform changes of the flexing action of the wrist in FIG. 12(C), the range of the fluctuations of acceleration detection values in vertical directions is larger in the tap operation, but the difference between the values is smaller than in the comparison between the tap operation and the turning action of the wrist. It is considered that the highly accurate distinction is difficult by the determination using the threshold value. However, as is known from the comparison between FIG. 12(A) and FIG. 12(C) on the equal scales of the horizontal axis (time), the period of the waveform is very long in the flexing action of the wrist compared to that in the tap operation. As described above, in the tap operation, a half period is about 10 to 13 ms, and a value corresponding to the amplitude of the waveform may be obtained using signal values within 10 to 13 ms. On the other hand, in the flexing action of the wrist, even when the signal values within 10 to 13 ms are used as shown in FIG. 12(C), the changes of the signal values in the period are very small and it is impossible to acquire a value corresponding to the amplitude. Namely, the waveform used for the detection of the tap operation is set for 10 to 13 ms (in a broad sense, a given period set based on the period of the waveform of the tap operation), and thereby, the tap operation and the flexing action of the wrist can be appropriately distinguished.

Therefore, the period and the threshold value used for the detection of the tap operation are appropriately set, and thereby, the tap operation can be detected without confusion with the similar actions.

3.3 Range of Sampling Frequency

As described above, in the detection of the tap operation, for distinction from the flexing action of the wrist, the waveform in a given period set based on the period of the waveform of the tap operation is to be processed. In this case, if the sampling frequency is set to be too low, there is a possibility that even one signal value is not acquired within the period, and it is impossible to perform the comparison processing with the threshold value in the first place. For example, when the sampling frequency equal to or less than 100 Hz as a frequency corresponding to 10 ms is used, if a certain period of 10 ms is to be sampled, there is a possibility that even one signal value is not acquired within the period to be sampled and the sampling frequency is inappropriate.

Figure 13:
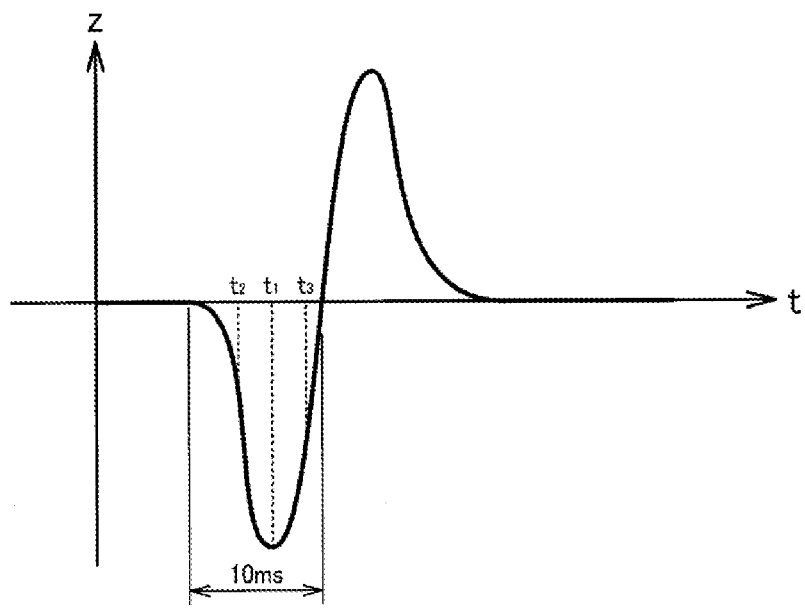
FIG. 13 is a diagram for explanation of differences of acceleration detection values depending on sampling times.

Further, the range of the acceleration detection values in the tap operation of about −6 G to +5.7 G described above using FIG. 12(A) corresponds to the minimum value and the maximum value (or values close thereto) of the fluctuations in vertical directions of the waveform. Accordingly, when the sampling frequency is low and the acceleration at the times corresponding to the minimum value or the maximum value is not acquired as an acceleration detection value, the acceleration detection values detected by the acceleration sensor 10 are smaller than the acceleration that the impact by the tap operation originally has. For example, when the original acceleration waveform of the tap operation is as shown in FIG. 13, at the above described sampling frequency of about 100 Hz, only one value can be acquired within 10 ms. Accordingly, if the time shown by t1 is the sampling time, desired processing may be performed, however, if the time of t2, t3, or the like is the sampling time, the acceleration detection value is smaller. As a result, the possibility that the acceleration detection values by the tap operation are smaller than about −2.4 G to +1.9 G as the range of changes of the acceleration detection values of the turning action of the wrist may not be denied and, in this case, in the determination processing using the above described threshold value, detection of the tap operation is impossible.

Figure 15A:
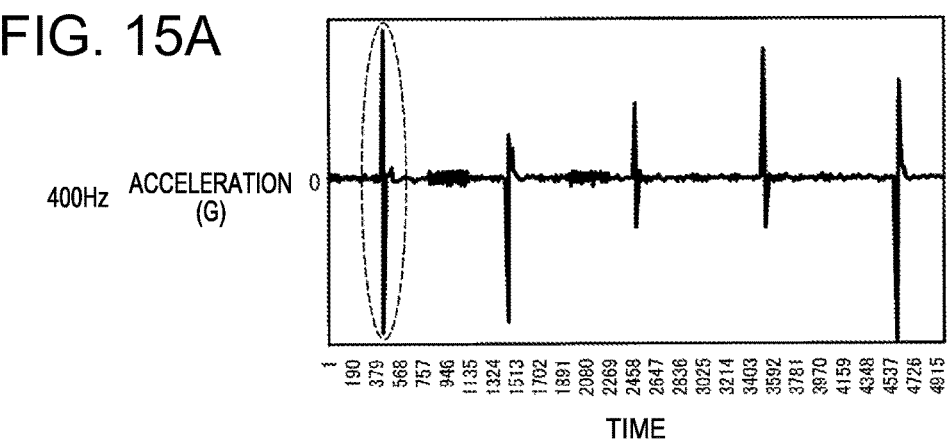
FIGS. 15(A) and 15(B) show waveform examples at an intermediate sampling frequency.
Figure 15B:
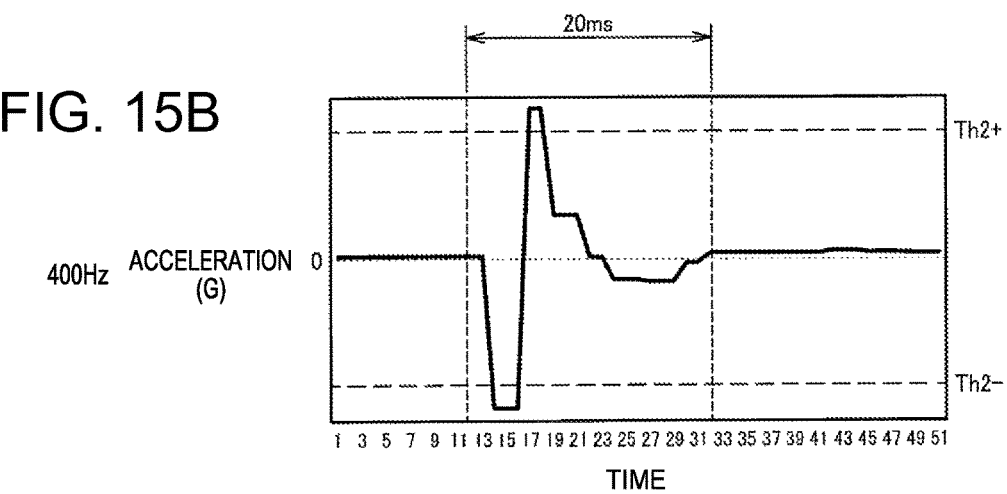
Figure 16A:
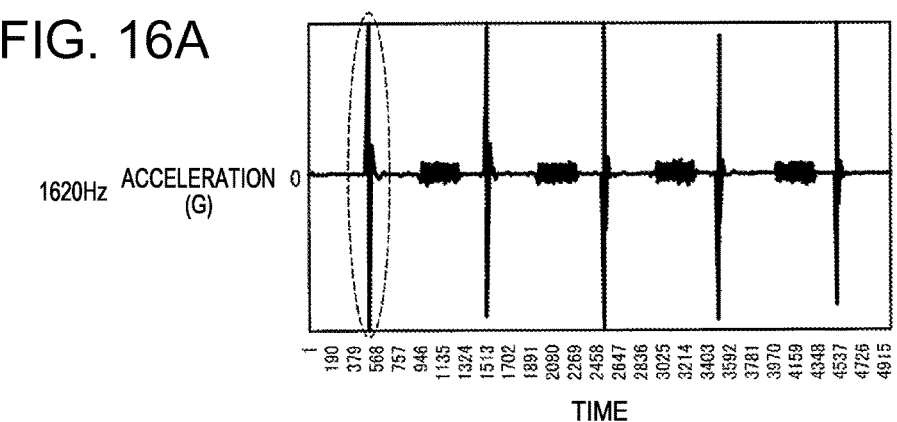
FIGS. 16(A) and 16(B) show waveform examples at a higher sampling frequency.
Figure 16B:
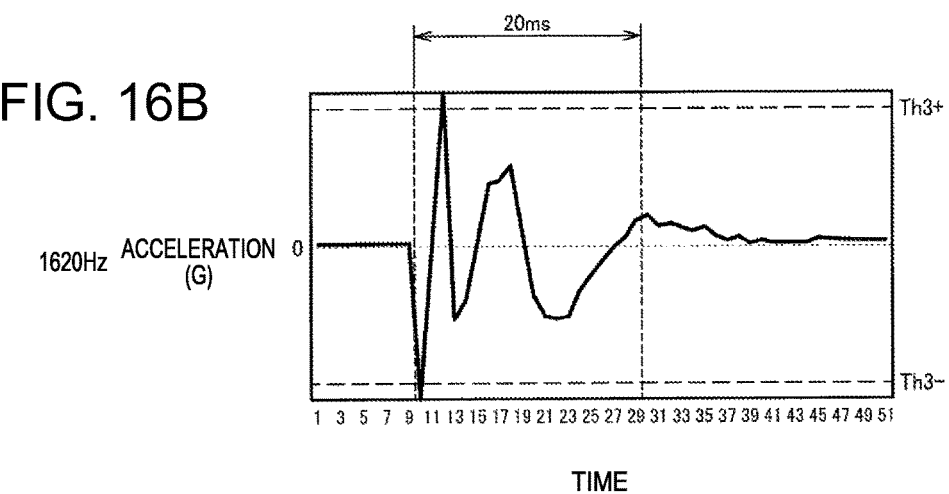

Namely, the detection accuracy of the tap operation depends on the possibility of sampling the apexes of the signal waveform or values close thereto. In other words, it is nothing else, but the higher the sampling frequency, the more improved the detection accuracy of the tap operation. FIGS. 14(A) to 16(B) show specific examples. FIG. 14(A) shows a waveform of acceleration detection values by the tap operation when the sampling frequency is set to 200 Hz, and FIG. 14(B) enlarges a part of FIG. 14(A). Similarly, FIGS. 15(A), 15(B) show signal waveforms by the tap operation at the sampling frequency of 400 Hz, and FIGS. 16(A), 16(B) show signal waveforms by the tap operation at the sampling frequency of 1620 Hz. Note that, in FIG. 14(B) etc., 20 ms corresponding to one period is to be sampled, and the way of thinking is the same when a half period is to be sampled.

As shown in FIG. 14(B), 200 Hz at which sampling of about two points for each peak is expected is used as the sampling frequency, and thereby, the fluctuations in vertical directions of the signal values in the period to be sampled can be detected to some extent. Specifically, the sampling frequency is set to 200 Hz, and thereby, the tap operation can be detected with accuracy of about 70%.

Further, as shown in FIG. 15(B), the sampling frequency is set to 400 Hz, and thereby, compared with the case of 200 Hz, the changes of the signal waveform within the period to be sampled can be acquired in more detail. Accordingly, regarding the absolute values of the maximum value, the minimum value of the acceleration detection values, the possibility of acquiring the larger values than those in the case of 200 Hz may be made higher and the possibility of false detection in the determination using the comparison processing with the threshold value may be suppressed. Specifically, the sampling frequency is set to 400 Hz, and thereby, the tap operation can be detected with accuracy of about 80%.

Similarly, as shown in FIG. 16(B), the sampling frequency is set to 1620 Hz, and thereby, compared with the case of 400 Hz, the more detailed signal waveform can be acquired. As shown in FIG. 16(B), at the sampling frequency of 1620 Hz, values as apexes of peaks can be acquired nearly reliably, and the values have absolute values larger than the minimum values, the maximum values at 400 Hz shown in FIG. 12(A) and FIG. 15(B). Namely, compared with the case of 400 Hz, the tap operation may be detected more reliably, and specifically, the tap operation can be detected with accuracy of nearly 100%.

4. Technique of Setting Sampling Frequency

As described above, the tap operation can be detected by setting the appropriate period to be processed (the tap determination period in FIG. 7(A)) and threshold value, and the detection accuracy is higher as the sampling frequency is set to be higher. However, the higher the sampling frequency, the larger the power consumption of the acceleration sensor 10. For example, the amount of current when the sampling frequency is 200 Hz is about 18 µA, and the amounts are 36 µA at 400 Hz and 100 µA at 1620 Hz.

Accordingly, in the embodiment, the sampling frequency is set in the setting unit 110 and the acceleration sensor 10 is operated using the set sampling frequency. Specifically, in the case where the possibility that the tap operation is performed is higher or the detection of the tap operation with higher accuracy is required, the sampling frequency is made higher. This is based on the consideration that the tap operation is one of user interfaces and, in the use case of the electronic apparatus, possibility that the tap operation is performed and the required accuracy can be estimated. As below, specific examples will be further explained.

4.1 Acquisition of Operation Information or Detection of Reception by Communication Unit As the time of setting the sampling frequency, the time when the operation information is acquired in the operation information acquisition unit 130 and the time when the reception of information is performed in the communication unit 150 are considered.

The time when the operation information is acquired is specifically the time when the user performs the operation of the operation unit 140. The operation of the operation unit 140 includes pressing down of buttons and keys, touching on the touch panel, or the like. Generally, these operations have lower possibilities of misoperation than the tap operation. This is because the buttons and keys have structures assumed to be physically pressed down and are provided in a partial area of the electronic apparatus, the user visually recognizes the buttons etc. and performs previously-defined operation, and thereby, misoperation is unlikely. Regarding the touch panel, the possibility of touching a different position from the intended position may not be denied, however, at least the operation based on the visual recognition by the user is expected. On the other hand, in the tap operation, which part of the electronic apparatus is tapped is not particularly limited. Accordingly, when an operation is performed in a situation in which it is impossible to visually recognize the electronic apparatus such that the wristwatch-type electronic apparatus is under the sleeve of the cloths or when an operation is performed without looking toward the electronic apparatus, misoperation without application of any sufficient impact may occur. Further, unlike the buttons etc., the way of operation (the position, the direction, the strength of tapping or the like) may vary among individuals, and differences may be caused even by the same user at each time of the operation.

On this account, when a series of operation including information input is performed, a use case where the tap operation is not performed at first, but input by key operation or the like is first operated, and then, the tap operation is performed may be highly likely.

For example, it is highly possible that the wristwatch-type electronic apparatus has a plurality of operation modes of an information display mode for displaying information of a clock or the like and an information input mode for inputting some information. In this case, when information input in the information input mode is stored or used for some processing in the electronic apparatus itself or the other systems. Accordingly, it is not preferable that the operation mode transitions to the information input mode without any intention of information input by the user and inappropriate information is input. In this case, it is preferable that switching of the operation mode from the information display mode to the information input mode is performed by the operation of the operation unit 140 with a lower possibility of misoperation and the tap operation is used in the information input after transfer to the information input mode. In such a use case, it is highly possible that the tap operation is performed after the operation of the operation unit 140, and it is preferable to set the sampling frequency to be higher.

Figure 17:
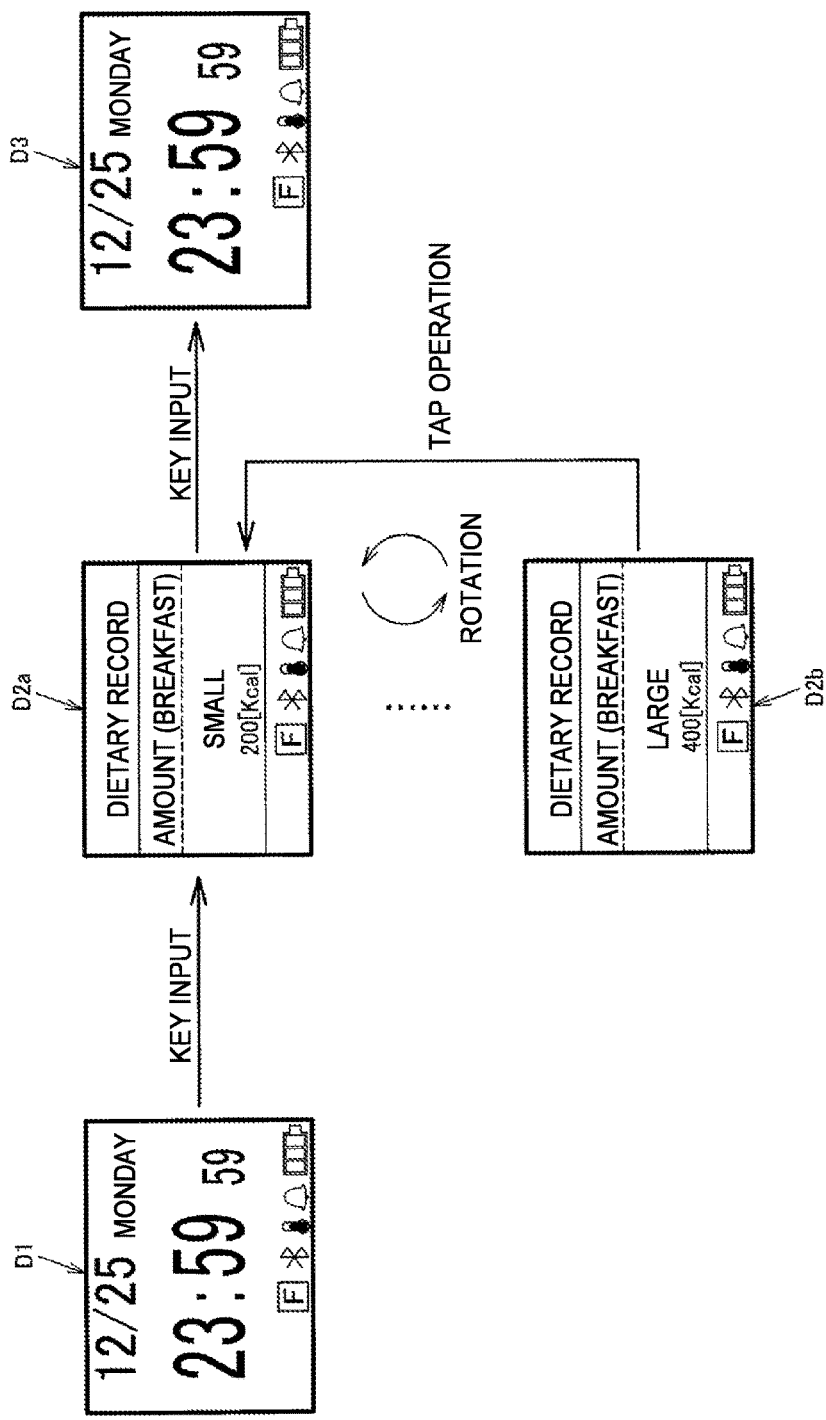
FIG. 17 shows a specific example of mode switching processing and screen transitions.

FIG. 17 shows a specific example of mode switching. The display screen shown by D1 in FIG. 17 corresponds to the information display mode and, here, displays information including date, time, remaining battery power, network environment. In the case of the information display mode for displaying D1, when operation information that a key operation in the operation unit 140 has been received is acquired, the processing unit 120 switches the operation mode to the information input mode, and, in response thereto, the display control unit 170 displays an information input screen on the display unit 180. The information input screen here is e.g. a screen shown by D2a and, in this example, information input on the amount of food intake as information on calorie intake is performed. As the amounts of food intake, a plurality of input candidates of "small", "medium", "large" are considered. In the example of FIG. 17, the tap operation is received at the phase and, at each time when the tap operation is received, the amount of food intake in the selected state is transitioned and the display screen is also transitioned in response thereto. For example, when there are two amounts of food intake of "small" and "large", the screens of D2a and D2b may be alternately displayed at each time of the tap operation, or when there are three or more amounts of food intake, they may be sequentially displayed. Note that, in the example of FIG. 17, misoperation is considered to be unfavorable with respect to the settling operation (determining operation) of the amount of food intake, and the settling operation is performed by key input. Namely, when acquisition of operation information is detected in the information input mode, mode switching processing to the information display mode is performed as shown by D3 (the same as D1).

Further, the case where the electronic apparatus cooperatively operates with another apparatus such as a smartphone is considered. For example, cooperation such that the electronic apparatus is operated using the operation unit of the smartphone, of detailed information held by the smartphone, part of simple information is transferred and displayed on the display unit 180 of the electronic apparatus, or the like is considered. More specifically, when the smartphone receives information of an electronic mail or the like, simple information of the electronic mail (information including a sender name, a title, time and date of the reception, etc.) or the mail text may be displayed in the electronic apparatus by operating the electronic apparatus. Or, when the smartphone detects an incoming call, turning off of the ringer or the like may be realized by the operation of the electronic apparatus.

In this case, some information from the smartphone including information representing reception of an electronic mail and an incoming call is received in the communication unit 150 of the electronic apparatus. Namely, the reception of the information in the communication unit 150 indicates a high possibility of the subsequent tap operation like the acquisition of the operation information in the operation information acquisition unit 130, and thus, when the reception of the information in the communication unit 150 is detected, it is preferable to set the sampling frequency to be higher. Particularly, in consideration of the above described turning off of the ringer or the like, more prompt operation is required, and the possibility of the tap operation that may be executed more easily than the key operation or the like is higher and the higher sampling frequency is significantly advantageous.

Note that it is preferable to restrict the setting of the higher sampling frequency in response to the acquisition of the operation information or the reception of the information in the communication unit 150 within a predetermined period. In this manner, increase in power consumption because the sampling frequency is higher in a long period may be suppressed. Further, when new acquisition of operation information or reception of information is detected in the predetermined period, the predetermined period may be set again at the detection time as a start. In this manner, returning to the lower sampling frequency despite of the higher possibility of the tap operation may be suppressed.

4.2 Distinction of Wearing State

Or, the sampling frequency may be set based on the wearing state of the electronic apparatus by the user. As described above, in the wearing determination unit 160, whether the wearing state or the non-wearing state of the electronic apparatus may be determined using the detection values in the photodiode 22 and the acceleration detection values of the acceleration sensor 10.

With respect to the wristwatch-type electronic apparatus, there is a high possibility that the operation for the electronic apparatus is performed in the wearing state, and, in the non-wearing state, there is a low possibility of operation. Particularly, with respect to the tap operation, for detection of the impact by tapping using the acceleration sensor 10, it is desirable that tapping is performed in a situation in which an impact is sufficiently transmitted such that the electronic apparatus is fixed to an arm or the like. The tap operation for the electronic apparatus grasped by a hand, the electronic apparatus placed on a desk, or the like is harder to be assumed.

Accordingly, when the electronic apparatus is in the non-wearing state, it is preferable to set the sampling frequency to be lower compared to that in the case of the wearing state. Note that the sampling frequency is not prevented from being set to a frequency at which the tap operation can be detected with a certain degree of accuracy, e.g., 200 Hz. For example, the frequency that has been 400 Hz or 1620 Hz in the wearing state may be set to 200 Hz. However, as described above, it is difficult to detect the tap operation in the non-wearing state, and the detection processing of the tap operation itself is not necessarily performed. Namely, the sampling frequency in the non-wearing state may be a frequency at which sufficient detection accuracy is not obtained e.g. below 200 Hz, and thereby, the lower power consumption can be realized.

4.3 Modified Examples

The setting time of the sampling frequency is not limited to those described above. For example, when the tap operation is detected at the lower sampling frequency, the sampling frequency may be made higher (in a narrow sense, 1620 Hz or the like, the maximum frequency in settings) in a predetermined period.

This is useful when e.g. a double-tap operation is detected. The double-tap operation refers to tap operations at twice in a short period like double-click in a mouse, the two tap operations are interpret as single user input and handled as input different from a single-tap operation. When the double-tap operation is acceptable, it is possible that, immediately after one tap operation, a tap operation is performed again, and the sampling frequency may be set to be higher for detection of the second tap operation. Particularly, according to the data analysis of the applicant, it is known that the acceleration detection values in the second tap operation of the double-tap operation are smaller than the acceleration detection values of the first tap operation and the single-tap operation. Therefore, the possibility of an erroneous determination becomes higher in the detection processing of the tap operation as the comparison processing with the threshold value, and it is desirable to make the sampling frequency higher for securement of sufficient detection accuracy.

Or, a behavior analysis of the user may be made and the sampling frequency may be set based on a result of the behavior analysis. Specifically, if the user is determined in a motion state, the sampling frequency is set to be higher than in the case of a determination of a non-motion state.

In the motion state, acceleration by the motion is contained in the acceleration detection values of the acceleration sensor 10, the rate of the signal values of the impacts by the tap operations occupied in the acceleration detection values becomes lower and the detection accuracy of the tap operation also becomes lower. Accordingly, in the motion state, it is desirable to make the detection accuracy higher by setting the sampling frequency to be higher.

As an example of the discrimination technique of the motion state, the acceleration detection values of the acceleration sensor 10 may be used and, when the acceleration detection values are larger than usual, the motion state may be determined Or, there is periodicity of motion in walking, running, or the like, and given periodicity is found in the acceleration detection values. Namely, whether the motion state or not may be determined from presence or absence of the periodicity of the acceleration detection values. Note that, regarding the behavior analysis of the user, various techniques are known and an arbitrary technique can be applied in the embodiment, and the more detailed explanation will be omitted.

5. Technique of Setting Threshold Value Cooperatively with Sampling Frequency In the above explanation, the sampling frequency is set in the setting unit 110, however, not limited to that. The setting unit 110 may change the sampling frequency and perform a setting of changing the threshold value of tap operation detection cooperatively with the sampling frequency.

Specifically, the setting unit 110 performs a setting such that, as the sampling frequency is set to be higher, the threshold value is higher. For example, when the sampling frequency is changed from F1 to F2 (>F1), the threshold value is changed from Th1 to Th2 (>Th1).

As described above, in order to appropriately detect the tap operation, discrimination processing from the turning action of the wrist is necessary. Further, acceleration due to motion or the like may be contained in the acceleration detection values as noise. In the embodiment, on the basis of the consideration that the acceleration detection values by the tap operation are larger than the acceleration detection values by the turning action of the wrist and noise, a value larger than the upper limit of the acceleration detection values assumed as the turning action of the wrist and noise is set as the threshold value. Note that a value smaller than the lower limit of the acceleration detection values assumed as the turning action of the wrist and noise is set as the threshold value for the acceleration detection values in the negative direction, however, that can be considered in the same way as the case in the positive direction using absolute values.

In the example of FIG. 12(B), since the absolute value of the acceleration detection value in the negative direction assumed in turning action is about 2.4 G, a value larger than that is set as a threshold value, and, if the absolute value of the detected acceleration detection value is larger than the threshold value, detection of a tap operation is determined. However, it is hard to consider that the same turning action of the wrist must be performed at every time, and the acceleration detection values vary for each action. Accordingly, it is difficult to determine the upper limit of the absolute value with respect to the acceleration detection values of the turning action. Accordingly, it is desirable that the threshold value is set with a certain degree of margin with respect to the values assumed to be acceleration detection values by the other actions than the tap operation. In the example of FIG. 12(B), if a threshold value of 2.5 G is set, acceleration detection values having larger absolute values may appear depending on the turning action, and, in this case, the turning action is falsely detected as a tap operation. Namely, in view of suppression of the possibility of false detection of the other actions than the tap operation as tap operations, it is more preferable that the absolute value of the threshold value is larger. For example, if about 4.0 G is used as the threshold value, the possibility of the false detection of the turning action as the tap operation can be made sufficiently lower.

However, as described above using FIGS. 14(A) to 16(B), as the sampling frequency is lower, the possibility that the values of the apexes of the peaks in the waveform can not be detected is higher, and, as a result, the possibility that the acceleration detection values are smaller is higher. Accordingly, if the absolute value of the threshold value is set to be too large, the acceleration detection values may not exceed the set threshold value despite of the tap operation, i.e., false detection of the tap operation as not the tap operation may be made.

In view of the above description, as long as the acceleration detection values tend to change in response to the sampling frequency, it is preferable to dynamically change the threshold value in response to the sampling frequency, not set the same threshold value for all sampling frequencies.

For example, when the sampling frequency is a sufficiently high frequency as 1620 Hz or the like, it is considered that the acceleration detection values by the tap operation are sufficiently large, and the threshold value is set to be a high value. In this manner, the possibility of the false detection of the other actions such as the turning action and noise than the tap operation as tap operations may be suppressed. For example, a value shown by Th3+ or Th3− in FIG. 16(B) may be set as the threshold value.

On the other hand, when the sampling frequency is a low frequency as 200 Hz or the like, to suppress the possibility of the false detection that the tap operation is detected as not the tap operation, the threshold value is set to a smaller value than that when the sampling frequency is higher. In this case, compared to the case of 1620 Hz or the like, the possibility of the false detection that the other actions than the tap operation as the tap operations is higher and that is accepted. This is because the situation that, although the user performs a tap operation with an explicit intention, the tap operation is not recognized by the electronic apparatus causes a lot of stress for the user and is not preferable. For example, as shown in FIG. 14(B), Th1+ or Th1− having the smaller absolute value than Th3+ or Th3− may be set as the threshold value.

Note that, at the intermediate sampling frequency of 400 Hz or the like, it is assumed that the acceleration detection values are intermediate values, and, for the threshold value, as shown in FIG. 15(B), Th2+ that satisfies Th1+<Th2+<Th3+, Th2− that satisfies |Th1−|<|Th2−|<|Th3−|, or the like may be used.

6. Specific Example of Embodiment

In the above described embodiment, as shown in FIG. 2, the electronic apparatus includes the setting unit 110 that sets the sampling frequency for acceleration detection of the acceleration sensor 10, the processing unit 120 that performs the determination of the tap operation based on the sensor information from the acceleration sensor, the operation information acquisition unit 130 that acquires the operation information from the operation unit 140, and the communication unit 150 that performs communication processing of information. Further, when reception of the information by the communication unit 150 is detected or when acquisition of the operation information by the operation information acquisition unit 130 is detected, the setting unit 110 sets the sampling frequency to F2 as a higher frequency than the sampling frequency F1 before detection.

Thereby, the sampling frequency can be made higher with the reception of the information by the communication unit 150 or the acquisition of the operation information as a trigger. As described above using FIG. 17 etc., when the reception of the information by the communication unit 150 or the acquisition of the operation information is performed, it is considered to be highly possible that the tap operation is subsequently performed. Accordingly, if it is considered that the tap operation is to be performed, the sampling frequency is appropriately made higher and the tap operation can be detected with high accuracy. To the contrary, in a situation in which the possibility of the tap operation is lower, the sampling frequency may be set to be lower and the power consumption can be reduced. Namely, according to the technique of the embodiment, the setting of the sampling frequency in consideration of the balance between the detection accuracy and the power consumption can be performed in response to the possibility of the tap operation.

Further, the electronic apparatus may include the biological information detection sensor 20 that detects the biological information as shown in FIG. 2. Then, the processing unit 120 performs correction processing with respect to the biological information from the biological information detection sensor 20 based on the body motion information as the sensor information from the acceleration sensor 10, and performs the determination of the tap operation based on the sensor information from the acceleration sensor 10.

Thereby, the acceleration sensor 10 can be used in common for both the reduction processing of body motion noise and the detection processing of the tap operation. It is known that the sensor information of the biological information detection sensor 20 (in a narrow sense, a pulse wave sensor) contains body motion noise due to motion of the user or the like. Therefore, in an electronic apparatus that performs detection of biological information such as a pulsimeter, as described above using FIGS. 5 and 6, generally, noise reduction processing based on the sensor information of the body motion sensor is performed. Further, in an electronic apparatus such as a wristwatch-type device, the tap operation is an useful interface as described above. Namely, in an arm mounted pulsimeter or the like, the tap operation is useful, and the tap operation can be detected using the acceleration sensor 10 as shown by the signal waveforms in FIG. 7(A) etc. Therefore, the technique of the embodiment is applied to the electronic apparatus such as the pulsimeter, and thereby, appropriate detection of the tap operation and removable of the body motion noise from the biological information can be realized by the common acceleration sensor 10, and reduction in space and cost or the like may be realized.

Further, the processing unit 120 may perform the mode switching processing of the operation mode of the electronic apparatus. Then, when the mode switching processing of switching the operation mode of the electronic apparatus from the first mode to the second mode is performed based on the operation information in the processing unit 120, the setting unit 110 performs a setting of changing the sampling frequency from F1 to F2.

Specifically, as shown in FIG. 17, the first mode may be the information display mode for displaying information and the second mode may be the information input mode for receiving external input of information. Then, when the mode switching processing of switching the operation mode of the electronic apparatus from the information display mode to the information input mode is performed based on the operation information in the processing unit 120, the setting unit 110 performs a setting of changing the sampling frequency from F1 to F2.

Thereby, the setting of the sampling frequency can be performed in response to the switching processing of the operation mode of the electronic apparatus. As described above, in comparison between the operation of the operation unit 140 such as key operation and the tap operation, the operation of the operation unit 140 has the advantage that the possibility of misoperation is lower than that of the tap operation and the tap operation has the advantage that the operation can be performed more easily than the operation of the operation unit 140. Note that, the phrase that the operation can be performed easily here means that the time from when the user intends an operation to when the operation is completed is shorter or the operation can be performed even when the electronic apparatus to be operated is not visually recognized by the user. Namely, the respective operations have different characteristics, and the situations in which the respective operations are used in use cases can be restricted to a certain degree. In the example of FIG. 17, as a trigger of the mode switching processing from the information display mode to the information input mode, the operation of the operation unit 140 with the lower possibility of misoperation is suitable, and, as an input interface in the information input mode, the tap operation that can be operated easily is suitable. Namely, the possibility of the tap operation may be determined in response to the operation mode, and establishment of the correspondence between the operation mode and the sampling frequency is useful.

Further, as shown in FIG. 2, the electronic apparatus may include the display control unit 170 that performs display control of the information in the display unit 180. Then, when the operation mode is the information input mode, the processing unit 120 performs a determination of the tap operation based on the sensor information from the acceleration sensor 10 at the sampling frequency of F2, and, if the tap operation is detected in the processing unit 120, the display control unit 170 performs display control of transitioning the displayed image displayed by the display unit 180.

Thereby, the tap operation can be used for screen transition and, concurrently, the sampling frequency can be set to be higher for the detection of the tap operation with high accuracy. The area of the display unit 180 is often restricted in a wristwatch-type device or the like, and it is impractical that a lot of information is contained in a single displayed image. As a result, as shown in the input screen of the amount of food intake of FIG. 17, it is considered to be natural that information is presented by preparing a plurality of displayed images and transitioning the screens among them. The electronic apparatus assumed in the embodiment has restricted numbers of buttons and keys, and thus, the types of operations that can be input are restricted and a complex operation such as transition from a given display screen to another arbitrary display screen is difficult. Accordingly, as shown in FIG. 17, the screen transition takes a form of selecting and displaying the sequentially arranged displayed images from the head one by one or the like, and it is highly possible to require a plurality of times of operations until desired screen display is obtained. Namely, in the information input mode, it is preferable to realize an interface for which a plurality of times of operations by the user are assumed, and, in this regard, the possibility of the tap operation that can be easily operated is sufficiently high.

Or, when the operation mode is the information input mode, acquisition of operation information is not detected and the tap operation is not detected in the processing unit 120 in a given period, the processing unit 120 performs mode switching processing of switching the operation mode from the information input mode to the information display mode, and the setting unit 110 performs a setting of changing the sampling frequency from F2 to F1.

Thereby, when operation or reception of information is not detected in a fixed period, the mode switching processing from the information input mode to the information display mode can be performed. As described above, the electronic apparatus assumed in the embodiment has the restricted number of buttons. If the mode switching processing is erroneously performed, unnecessary information input may be performed or information in the middle of the performance may be cancelled and input data may be lost, and accordingly, the processing is preferably performed based on the operation of the operation unit 140. However, the case where the restriction of the number of buttons is very strong and only one type of the operation input by the operation unit 140 can be performed (e.g. there is only one button or key) is considered. In this case, the mode switching from the information display mode to the information input mode and the mode switching of returning to the information display mode after information input is completed and the input information is settled and stored may be performed by the operation of the operation unit 140. However, when the user erroneously performs the mode switching processing from the information display mode to the information input mode, it is impossible to realize the mode switching processing of returning to the information display mode without settlement of information input. In this case, it is inappropriate to force the user to perform an operation of once inputting unnecessary information, and then, deleting the information. Accordingly, in the embodiment, the user may exit the information input mode with a trigger that the operation is not detected in a fixed period. In this manner, a user-friendly interface can be realized. Note that various modifications may be made to the trigger of the mode switching processing from the information input mode to the information display mode. For example, in addition to the above described condition, when reception of information by the communication unit 150 is not detected, the mode switching processing to the information display mode may be performed.

In the above described embodiment, as shown in FIG. 2, the electronic apparatus includes the setting unit 110 that sets the sampling frequency for the acceleration detection of the acceleration sensor 10, the processing unit 120 that performs the determination of the tap operation based on the sensor information from the acceleration sensor 10, and the wearing determination unit 160 that determines the wearing state of the electronic apparatus. Then, when the wearing determination unit 160 determines that the electronic apparatus is in the non-wearing state, the setting unit 110 sets the sampling frequency to F1 lower than the sampling frequency F2 before the determination.

Thereby, the setting of the sampling frequency can be performed based on the determination result of the wearing state of the electronic apparatus. The non-wearing state corresponds to e.g., with a wristwatch-type electronic apparatus, a state in which the belt is detached. Accordingly, the state in which the belt is detached and the apparatus is grasped by a hand of the user is the non-wearing state and the state in which the apparatus is completely apart from the hand of the user and left on a desk or the like is the non-wearing state. In either case, in the non-wearing state, it is difficult to detect the impact by the tap operation of the user by the acceleration sensor 10, and it may be determined that the possibility of the tap operation is low. Further, this technique is the same as the above described technique using the operation information and the reception status in the communication unit 150 in that, when the possibility of the tap operation is lower, the sampling frequency may be made lower.

In the above described embodiment, as shown in FIG. 2, the electronic apparatus includes the setting unit 110 that sets the sampling frequency for the acceleration detection of the acceleration sensor 10 and sets the threshold value for the determination of the tap operation, and the processing unit 120 that performs the determination of the tap operation based on the sensor information from the acceleration sensor 10. Then, the setting unit 110 sets the sampling frequency to F1 and sets the threshold value to Th1 in the first set mode of the acceleration sensor 10, and sets the sampling frequency to F2 as the higher frequency than F1 and sets the threshold value to Th2 as the larger value than Th1 in the second set mode of the acceleration sensor 10.

Here, the threshold value for the determination of the tap operation is a value used for comparison processing with the peak value of the acceleration detection values as shown by Th1+ etc. in FIG. 7(A) and FIG. 14(B). Note that the detection processing of the tap operation may use the downward change of the waveform as described above, the upward change, or both of them. In this case, suppose that the reference value of the waveform (the center of the vertical axis in FIG. 7 etc.) is 0 G, the acceleration detection values in the upward direction take positive values and the acceleration detection values in the downward direction take negative values, however, the magnitude of the threshold value may be considered as the magnitude of the fluctuation range with respect to the reference value. Namely, it may be considered that the threshold value having the larger difference from the reference value takes the larger value, and, when the reference value of the waveform is 0 G as described above, the threshold value of the embodiment may be considered using the absolute values of the acceleration detection values.

Thereby, the threshold value can be appropriately set in response to the sampling frequency. Specifically, as shown in FIG. 16(B), if the sampling frequency is higher and the waveform of the acceleration detection values correctly reflects the acceleration waveform due to the impact by the tap operation, the threshold value may be set to be larger and the possibility of the false detection of the other actions than the tap operation as tap operations may be suppressed. On the other hand, as shown in FIG. 14(B), if the waveform of the acceleration detection values is coarse with respect to the acceleration waveform due to the impact by the tap operation, the threshold value may be set to be lower and the possibility of the false detection of the tap operation as not the tap operation may be suppressed.

Further, when the user wearing the electronic apparatus is determined to be in the motion state, the setting unit 110 may set the set mode of the acceleration sensor 10 to the second set mode.

Thereby, when the user is determined to be in the motion state, the sampling frequency and the threshold value can be set to be higher. In the motion state, the sensor information from the acceleration sensor 10 contains noise due to the motion, however, as shown in FIG. 16(B), the threshold value may be set to be higher and the acceleration detection values due to the noise and the tap operation may be distinguished with high accuracy.

Further, the setting unit 110 may set the first set mode in the information display mode for displaying information and set the second set mode in the information input mode for receiving external input of information.

Thereby, in the information display mode and the information input mode, the sampling frequencies and the threshold values suitable for the respective modes can be set. Like the use case shown in FIG. 17, the case where the possibility of the tap operation is higher in the information input mode than that in the information display mode is highly likely. Accordingly, in the information input mode, the second set mode is set to enable the tap operation detection with high accuracy. On the other hand, in the information display mode with the lower possibility of the tap operation, the first set mode at the lower sampling frequency is set, and reduction of power consumption etc. can be realized.

Further, as shown in FIG. 2, the electronic apparatus may include the display control unit 170 that performs display control of the information in the display unit 180. Then, when the acceleration sensor 10 is set in the second set mode corresponding to the information input mode by the setting unit 110, the processing unit 120 performs a determination of the tap operation based on the sensor information from the acceleration sensor 10 in which the sampling frequency is set to F2 and the threshold value is set to Th2, and, if the tap operation is detected in the processing unit 120, the display control unit 170 performs display control of transitioning the displayed image displayed by the display unit 180.

Thereby, the tap operation can be used for screen transition and, concurrently, the second set mode at the higher sampling frequency can be set for the detection of the tap operation with high accuracy. The area of the display unit 180 is often restricted in a wristwatch-type device or the like, and it is impractical that a lot of information is contained in a single displayed image. As a result, as shown in the input screen of the amount of food intake of FIG. 17, it is considered to be natural that information is presented by preparing a plurality of displayed images and transitioning the screens among them. The electronic apparatus assumed in the embodiment has restricted numbers of buttons and keys, and thus, the types of operations that can be input are restricted and a complex operation such as transition from a given display screen to another arbitrary display screen is difficult. Accordingly, the screen transition takes a form of selecting and displaying the sequentially arranged displayed images from the head one by one or the like as shown in FIG. 17, and it is highly possible to require a plurality of times of operations until a desired screen is displayed. Namely, in the information input mode, it is preferable to realize an interface for which a plurality of times of operations by the user are assumed, and, in this regard, the possibility of the tap operation that can be easily operated is sufficiently high.

Further, the processing unit 120 may perform a determination of the tap operation based on at least one comparison processing of comparison processing between the signal value in the positive direction in the predetermined axis directions (if the Z-axis shown in FIG. 3 is considered, in a narrow sense, in the upward direction) of the acceleration sensor 10 and Th+ as the threshold value in the positive direction and comparison processing between the signal value in the negative direction in the predetermined axis directions (if the Z-axis shown in FIG. 3 is considered, in a narrow sense, in the downward direction) of the acceleration sensor and Th− as the threshold value in the negative direction.

Thereby, as described above using FIG. 7(A) etc., the determination of the tap operation can be performed based on the comparison processing between the fluctuations in vertical directions of the acceleration detection values and the threshold value. Note that, here, Th+ and Th− are separately described, however, two kinds of threshold values are not necessarily set. For example, the threshold value may be information corresponding to the absolute value as described above, and accordingly, one threshold value Th as a positive value may be set, and comparison processing with Th may be performed with respect to the signal values in the positive direction and comparison processing with −Th (or comparison processing between absolute values of the negative signal values and Th) may be performed with respect to the signal values in the negative direction. Note that, as described above in the explanation using FIG. 12(A), when the acceleration detection values in the positive direction and the negative direction are compared, the values in the negative direction corresponding to the impact direction of the tap operation are often only slightly larger than the values in the positive direction corresponding to the opposite direction to the impact direction. In consideration of the differences, different threshold values may be set for the positive direction and the negative direction.

Further, as shown in FIG. 2, the electronic apparatus may include the wearing determination unit 160 that determines the wearing state of the electronic apparatus. Then, when the wearing determination unit 160 determines that the electronic apparatus is in the non-wearing state, the setting unit 110 sets the acceleration sensor 10 in a third set mode with the value of the sampling frequency F0 lower than F1.

Thereby, the setting of the sampling frequency can be performed based on the determination result of the wearing state of the electronic apparatus. The non-wearing state corresponds to e.g., with a wristwatch-type electronic apparatus, a state in which the belt is detached. Accordingly, the state in which the belt is detached and the apparatus is grasped by a hand of the user is the non-wearing state and the state in which the apparatus is completely apart from the hand of the user and left on a desk or the like is the non-wearing state. In either case, in the non-wearing state, it is difficult to detect the impact by the tap operation of the user by the acceleration sensor 10, and it may be determined that the possibility of the tap operation is low and the sampling frequency is set to be lower.

Note that the acceleration sensor 10 is set in the third set mode in the non-wearing state because e.g. an embodiment in which the first set mode is set in the information display mode and the second set mode is set in the information input mode is assumed. In the information display mode, although the possibility of the tap operation is lower than that in the information input mode, it is not absolute that there is no tap operation, and it is desirable that the tap operation can be detected even with relatively low accuracy. For example, in the first set mode, the detection accuracy of about 70% may be secured at the sampling frequency of about 200 Hz. On the other hand, in the non-wearing state, as described above, the problem is not significant even when it is completely impossible to detect the tap operation, and the sampling frequency as high as that in the information display mode is not required. Namely, the sampling frequency smaller than 200 Hz is acceptable, and the third set mode different from the first set mode is set in the non-wearing state. In this case, the detection of the tap operation is unnecessary in the first place, and the threshold value for the tap operation detection is not necessarily set.

Note that the embodiment has been explained in detail as described above, however, a person who skilled in the art could readily understand that many modifications may be made without substantially departing from the new matter and effects of the invention. Therefore, the modified examples may fall within the scope of the invention. For example, in the specification or drawings, the terms described with the broader or synonymous different terms at least once may be replaced by the different terms in any part of the specification or drawings. Further, the configurations and operations of the electronic apparatus are not limited to those explained in the embodiment, but various modifications may be made.

The invention claimed is:

1. An electronic apparatus comprising:
   a setting unit that sets a sampling frequency for acceleration detection of an acceleration sensor;
   a processing unit that performs a determination of a tap operation based on sensor information from the acceleration sensor;
   an operation information acquisition unit that acquires operation information from an operation unit;
   a communication unit that performs communication processing of information; and
   a biological information detection sensor that detects biological information,
   wherein, when reception of the information by the communication unit is detected or when acquisition of the operation information by the operation information acquisition unit is detected, the setting unit sets the sampling frequency to F2 as a higher frequency than the sampling frequency F1 before detection, and
   wherein the processing unit performs correction processing on biological information from the biological information detection sensor based on body motion information as the sensor information from the acceleration sensor, and performs a determination of the tap operation based on the sensor information from the acceleration sensor.

2. The electronic apparatus according to claim 1, wherein the processing unit performs mode switching processing of an operation mode of the electronic apparatus, and
   the setting unit performs a setting of changing the sampling frequency from F1 to F2 when the mode switching processing of switching the operation mode of the electronic apparatus from a first mode to a second mode based on the operation information in the processing unit.

3. The electronic apparatus according to claim 2, wherein the first mode is an information display mode for displaying information,
   the second mode is an information input mode for receiving external input of information, and
   the setting unit performs a setting of changing the sampling frequency from F1 to F2 when the mode switching processing of switching the operation mode of the electronic apparatus from the information display mode to the information input mode based on the operation information in the processing unit.

4. The electronic apparatus according to claim 3, further comprising a display control unit that performs display control of information in a display unit,
   wherein, when the operation mode is the information input mode, the processing unit performs a determination of the tap operation based on the sensor information from the acceleration sensor in which the sampling frequency is set to F2, and the display control unit performs the display control of transitioning a displayed image displayed on the display unit when the tap operation is detected in the processing unit.

5. The electronic apparatus according to claim 3, wherein, when the operation mode is the information input mode and acquisition of the operation information is not detected and the tap operation is not detected in the processing unit for a given period, the processing unit performs the mode switching processing of switching the operation mode from the information input mode to the information display mode, and the setting unit performs a setting of changing the sampling frequency from F2 to F1.

6. An electronic apparatus comprising:
   a setting unit that sets a sampling frequency for acceleration detection of an acceleration sensor;
   a processing unit that performs a determination of a tap operation based on sensor information from the acceleration sensor; and
   a wearing determination unit that determines a wearing state of the electronic apparatus,
   wherein, when the electronic apparatus is determined to be in a non-wearing state, the setting unit sets the sampling frequency to F1 as a lower frequency than the sampling frequency F2 before determination.

7. An electronic apparatus comprising:
   a setting unit that sets a sampling frequency for acceleration detection of an acceleration sensor and a threshold value for determination of a tap operation; and
   a processing unit that performs a determination of the tap operation based on sensor information from the acceleration sensor,
   wherein the setting unit sets the sampling frequency to F1 and sets the threshold value to Th1 in a first set mode of the acceleration sensor, and sets the sampling frequency to F2 as a higher frequency than F1 and sets the threshold value to Th2 as a larger value than Th1 in a second set mode of the acceleration sensor.

8. The electronic apparatus according to claim 7, further comprising a biological information detection sensor that detects biological information,
   wherein the processing unit performs correction processing on biological information from the biological information detection sensor based on body motion information as the sensor information from the acceleration sensor, and performs a determination of the tap operation based on the sensor information from the acceleration sensor.

9. The electronic apparatus according to claim 7, wherein the setting unit sets the set mode of the acceleration sensor to the second set mode when a user wearing the electronic apparatus is in a motion state.

10. The electronic apparatus according to claim 7, wherein the setting unit sets the first set mode in an information display mode for displaying information, and sets the second set mode in an information input mode for receiving external input of information.

11. The electronic apparatus according to claim 10, further comprising a display control unit that performs display control of information in a display unit,
wherein, when the acceleration sensor is set in the second set mode corresponding to the information input mode by the setting unit, the processing unit performs a determination of the tap operation based on the sensor information from the acceleration sensor in which the sampling frequency is set to F2 and the threshold value is set to Th2, and the display control unit performs the display control of transitioning a displayed image displayed on the display unit when the tap operation is detected in the processing unit.

12. The electronic apparatus according to claim 7, wherein the processing unit performs a determination of the tap operation based on at least one comparison processing of comparison processing between a signal value in a positive direction in predetermined axis directions of the acceleration sensor and Th+ as the threshold value in the positive direction and comparison processing between the signal value in a negative direction in the predetermined axis directions of the acceleration sensor and Th− as the threshold value in the negative direction.

13. The electronic apparatus according to claim 7, further comprising a wearing determination unit that determines a wearing state of the electronic apparatus,
wherein, when the electronic apparatus is determined to be in a non-wearing state, the setting unit sets the acceleration sensor in a third set mode in which a value of the sampling frequency is F0 as a lower frequency than F1.

14. A method of detecting a tap operation comprising:
performing setting processing of setting a sampling frequency for acceleration detection of an acceleration sensor;
performing tap determination processing of determining a tap operation based on sensor information from the acceleration sensor with the set sampling frequency;
detecting biological information with a biological information detection sensor; and
performing correction processing on biological information from the biological information detection sensor based on body motion information as the sensor information from the acceleration sensor,
as the setting processing, when reception of the information by a communication unit is detected or when acquisition of operation information is detected, performing processing of setting the sampling frequency to F2 as a higher frequency than the sampling frequency F1 before detection.

15. A method of detecting a tap operation comprising:
performing setting processing of setting a sampling frequency for acceleration detection of an acceleration sensor and a threshold value for determination of a tap operation; and
performing tap determination processing of determining a tap operation based on sensor information from the acceleration sensor with the set sampling frequency and threshold value,
as the setting processing, performing processing of setting the sampling frequency to F1 and setting the threshold value to Th1 in a first set mode of the acceleration sensor, and setting the sampling frequency to F2 as a higher frequency than F1 and setting the threshold value to Th2 as a larger value than Th1 in a second set mode of the acceleration sensor.

16. An electronic apparatus comprising:
a setting unit that sets a sampling frequency for acceleration detection of an acceleration sensor;
a processing unit that performs a determination of a tap operation based on sensor information from the acceleration sensor; and
a communication unit that performs communication processing of information,
wherein, when reception of the information by the communication unit is detected, the setting unit sets the sampling frequency to F2 as a higher frequency than the sampling frequency F1 before detection.

* * * * *